United States Patent [19]

McPherson et al.

[11] Patent Number: 6,013,855
[45] Date of Patent: Jan. 11, 2000

[54] GRAFTING OF BIOCOMPATIBLE HYDROPHILIC POLYMERS ONTO INORGANIC AND METAL SURFACES

[75] Inventors: Timothy McPherson, Lafayette; Kinam Park; Seongbong Jo, both of West Lafayette, all of Ind.

[73] Assignee: United States Surgical, Norwalk, Conn.

[21] Appl. No.: 08/774,707

[22] Filed: Dec. 26, 1996

Related U.S. Application Data

[60] Provisional application No. 60/023,360, Aug. 6, 1996.

[51] Int. Cl.$^7$ .................................................. A61F 2/02
[52] U.S. Cl. ............................. 623/11; 600/36; 427/2.24; 427/2.25
[58] Field of Search ................................ 623/11; 600/36; 427/2.24, 2.25

[56] References Cited

U.S. PATENT DOCUMENTS

| | | |
|---|---|---|
| 3,519,538 | 7/1970 | Messing et al. . |
| 3,642,761 | 2/1972 | Ohira et al. . |
| 4,365,359 | 12/1982 | Raab .......................................... 623/16 |
| 4,652,459 | 3/1987 | Engelhardt ................... 623/16 |
| 4,748,121 | 5/1988 | Beaver et al. . |
| 5,275,838 | 1/1994 | Merrill . |
| 5,356,433 | 10/1994 | Rowland et al. . |
| 5,453,467 | 9/1995 | Bamford et al. . |
| 5,512,492 | 4/1996 | Herron et al. ........................... 436/518 |
| 5,782,908 | 7/1998 | Cahalan et al. ............................. 623/1 |

FOREIGN PATENT DOCUMENTS

WO94/21386  9/1994  WIPO .

OTHER PUBLICATIONS

Desai, N. et al., *J. Biomed. Mater. Res.* 25: 829–843, 1991.
Rollason, G. et al., *J. Biomed. Mater. Res.* 26: 675–693, 1992.
Llanos, G.R. et al., *J. Biomed. Mater. Res.* 27: 1383–1391, 1993.
Osterberg, E. et al., *Colloids Surfaces A: Physicochem. Eng. Aspects* 77: 159–169, 1993.
Maechling–Strasser, C. et al., *J. Biomed. Mater. Res.* 23: 1395–1410, 1989.
Lopez, G. P. et al., *J. Biomed. Mater. Res.* 26: 415–439, 1992.
Ishihara, K. et al., *J. Polym. Sci. Part A: Polym. Chem.* 30: 929–932, 1992.
Lee, J. et al., *J. Colloid Interface Sci.* 131: 252–266, 1989.
Tseng, Y.–C. et al., *J. Biomed. Mater. Res.* 26: 373–391, 1992.
Tseng, Y.–C. et al., *Biomaterials* 14: 392–400, 1993.
Tseng, Y.–C. et al. *J. Biomat. App.* 7: 233–249, 1993.
Amiji, M. et al. *Biomaterials* 682–692, 1992.
Amiji, M. et al.,*J. Colloid Interface Sci* 155: 251–255, 1993.
Maechling–Strasser, C. et al., *J. Biomed. Mater. Res.* 23: 1385–1393, 1989.
Norman, M. E. et al., *J. Biomed. Mater. Res.* 27: 861–866, 1993.

(List continued on next page.)

*Primary Examiner*—Paul B. Prebilic

[57] ABSTRACT

Methods for grafting unmodified PEO or any other water-soluble polymers to the surfaces of metals and glasses to form biocompatible surfaces having low protein affinity is provided. One technique includes the steps of: (a) providing a support member having a plurality of hydroxyl or oxide groups attached to a surface of said support member; (b) exposing said surface to a silane coupling agent to cause the silane coupling agent to form a silane layer that is covalently bound to the surface wherein the silane layer comprises a plurality of vinyl groups; and (c) exposing the silane layer to a hydrophilic polymer and causing the silane layer to react with the hydrophilic polymer to covalently bond to the silane layer. Exposure of the silane layer to γ-radiation to induce grafting with low radiation to induce grafting of the hydrophilic polymer to the silane layer. Another technique comprises grafting a silylated hydrophilic polymer or chain having a hydrophobic domain directly to the metal or inorganic surface.

16 Claims, 8 Drawing Sheets

OTHER PUBLICATIONS

Gingell, D. et al., *J. Biomed. Mater. Res.* 28: 491–503, 1994.
Amiji, M. et al., *J. Biomater. Sci. Polymer Edn.* 3: 375–388, 1992.
Yasuda, H. *Plasma Polymerization*, Academic Press: Orlando, Fl, 1985; pp. 432.
Kiaei, D. et al., *J. Biomed. Mater Res.* 26: 357–372, 1992.
Fujimoto, K. et al., *J. Biomed. Mater. Res.* 27: 1559–1567, 1993.
Tsubokawa, N. *Prog. Polym. Sci.* 17: 417–470, 1992.
Tsubokawa, N. et al., *J. Polym. Sci. Pt. A: Polym. Chem.* 30: 561–567, 1992.
Browne, T. et al., *J. App. Polym. Sci.* 44: 671–677, 1992.
Mathew, J. et al., *Polymer Journal* 24: 31–41, 1992.
Uchida, E. et al., *J. App. Polym. Sci.* 47: 417–424, 1993.
Wheals, B. B. *J. Chromatography* 107: 402–406, 1975.
Ferguson, G. S. et al., *Macromolecules* 26: 5870–5875, 1993.
Papirer, E. et al., *Chromatographia* 23: 639–647, 1987.
Pathmamanoharan, C. *Colloids Surfaces* 50: 1–6, 1990.
Lin, S. C. et al., *J. Biomed. Mater. Res.* 25: 791–795, 1991.
Sukenik, C. N. et al., *J. Biomed. Mater. Res.* 24: 1307–1323, 1990.
Vandenberg, E. et al., *J. Colloid Interface Sci.* 143: 327–335, 1991.
Dunkirk, S. G. et al., *J. Biomater. Appl.* 6: 131–156, 1991.
Tseng, Y.–C. et al., *Biomaterials* 16: 963–972, 1995.
Kamath, K. et al., *J. Appl. Biomater.* 5: 163–173, 1994.
Kamath, K. et al., *Colloids Surfaces B: Bioint.* 2: 471–479, 1994.
Arkles, B. in *Silicon compounds: register and review 5th edition*, Anderson, R., Larson, G. L., and Smith, C., Ed.; Hüls America: Piscataway, NJ, 1991; vol. 50–64.
Chvalovsky, V. in *Carbon–functional organosilicon compounds*, Chvalovsky, V., and Bellama, J., Ed.; Plenum Press: New York, 1984; vol. 1–33.
Silberzan, P. et al., *Langmuir* 7: 1647–1651, 1991.
Ishida, H. et al., *J. Polym. Sci.: Polym. Phys. Ed.* 18: 1931–1943, 1980.
Plueddemann, E. *Silane coupling agents, second edition*, Plenum Press: New York, 1991; pp. 253.
Wirth, M. J. et al., *Anal. Chem.* 65: 822–826, 1993.
Ruhe, J. et al., *Langmuir* 9: 2383–2388, 1993.
Sun, F. et al.: *Colloids and Surfaces A: Physicochemical and Engineering Aspects*, 93: 191–200, 1994.
Sun, F. et al.: *Langmuir* 9: 3200–3207, 1993.
Sun. F. et al.: *Macromolecules* 27: 3053–3062, 1994.
Sun, F. et al.: *J. Vac, Sci. Technol. A* 12: 2499–2506, 1994.
Sun, F. et al.: *J. Am. Chem. Soc.* 118: 1856–1866, 1996.
Sartore, L. et al., *J. of Bioactive and Compatible Polymers* 9: 411–428, 1994.
Topchiyeva, I.N., *Popular Sci. U.S.S.R.* 32: 833–851, 1990.
Harris, J.M. et al., *J. of Polymer Science* 22: 341–352, 1984.
Zalipsky, S. et al., *Eur. Polym. J.* 19: 1177–1183, 1983.
Mutter, M. *Tetrahedron Letters* 31: 2839–2842, 1978.
Bailey, D. et al., *J. Macromol. Sci. Chem.* A12(5): 661–699, 1978.
Nagasaki, Y. et al., *Trip* 4(2): 59–64, 1996.

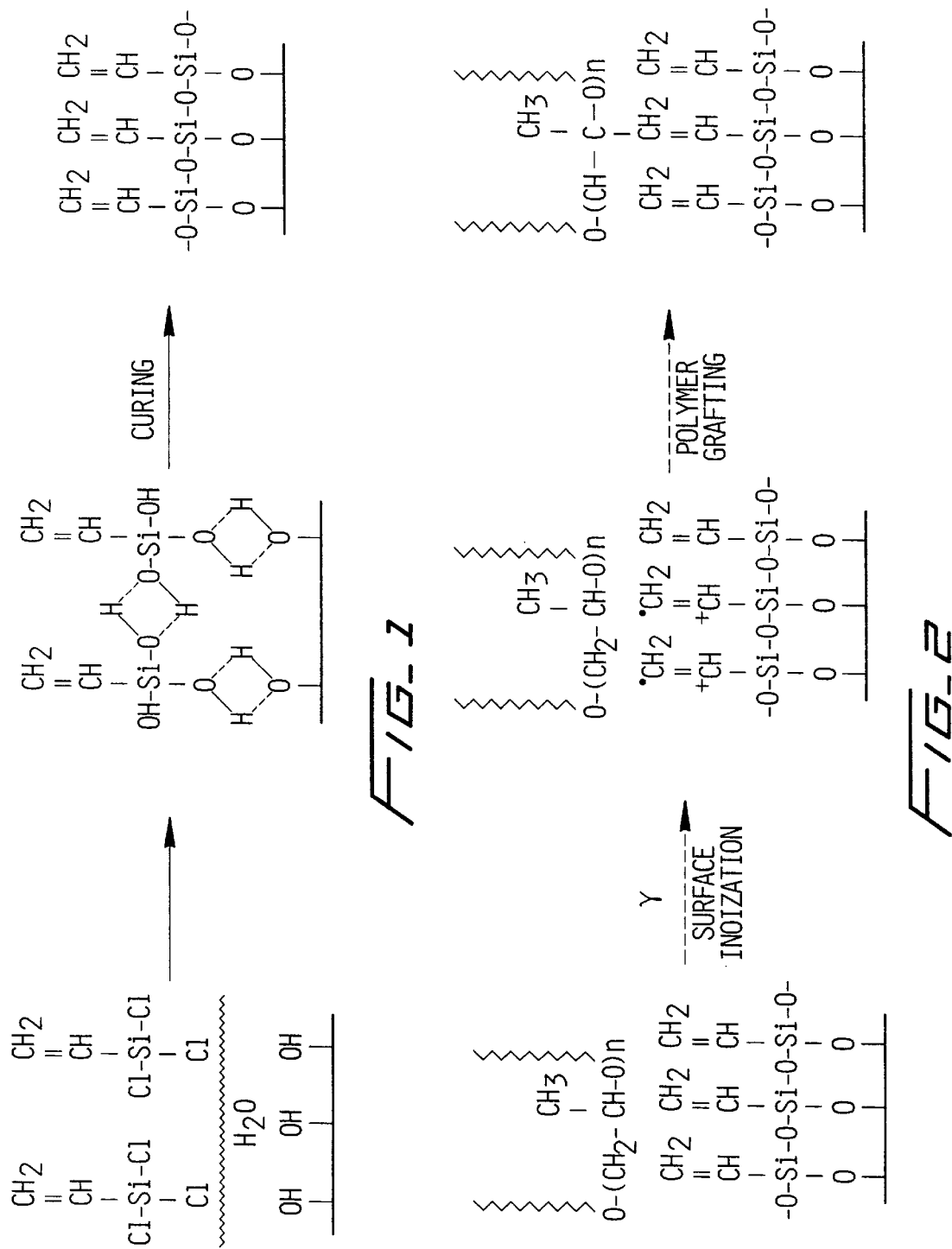

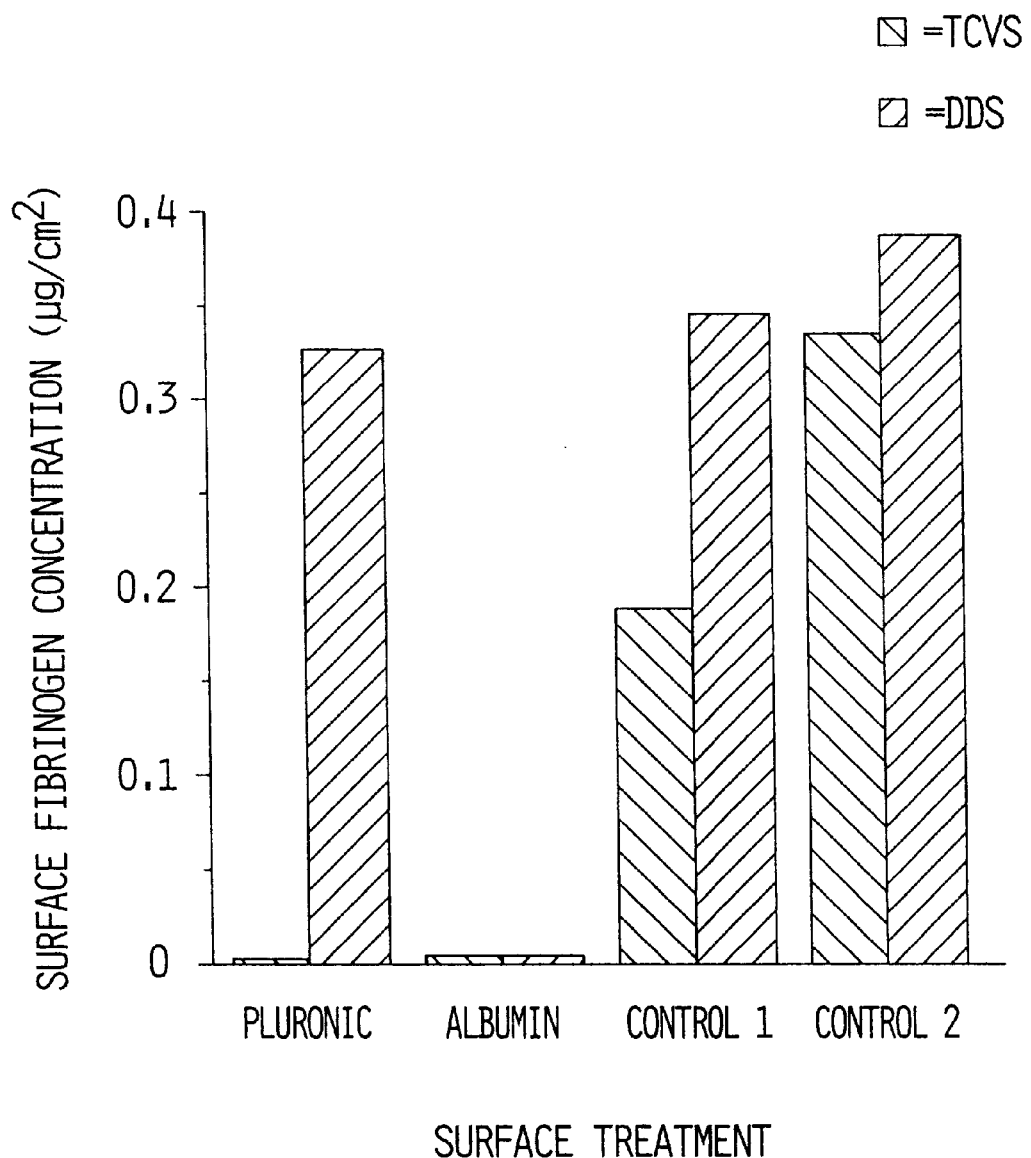
FIG_3

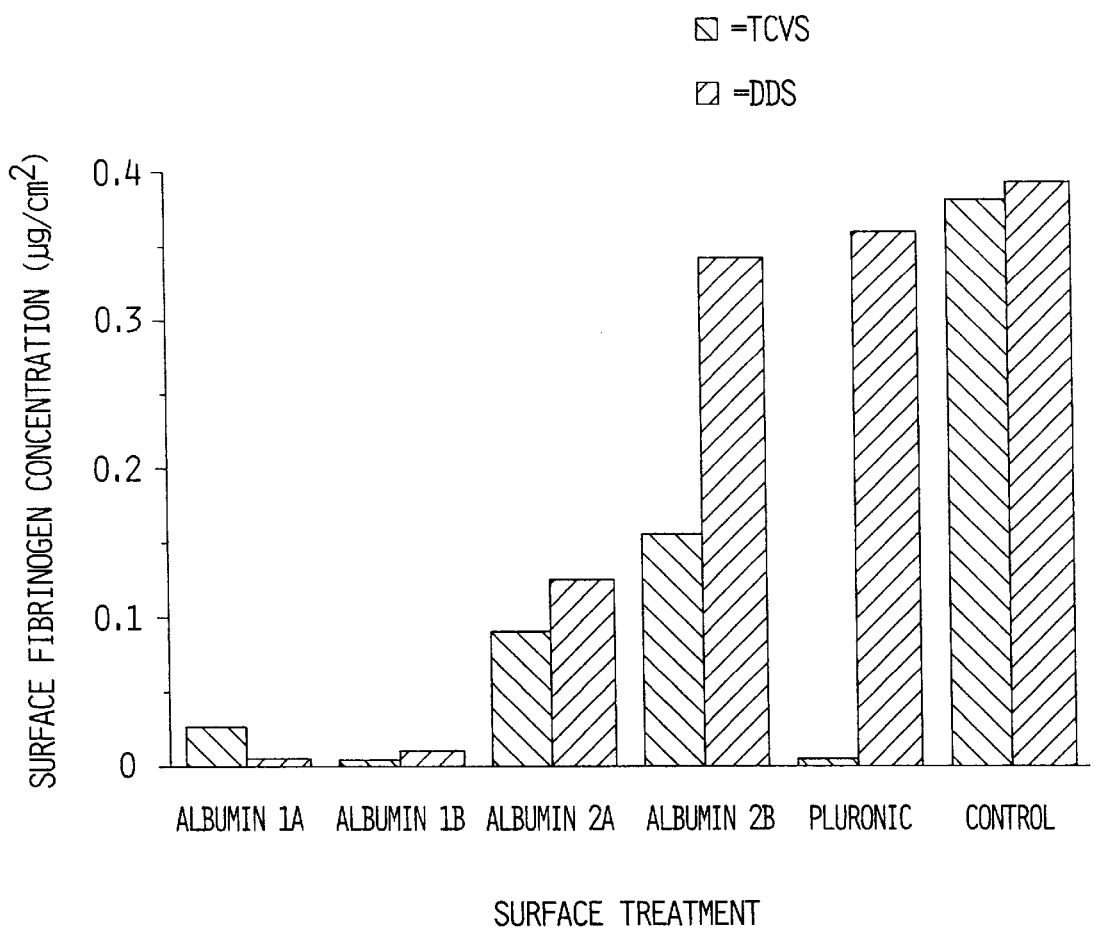
FIG_4

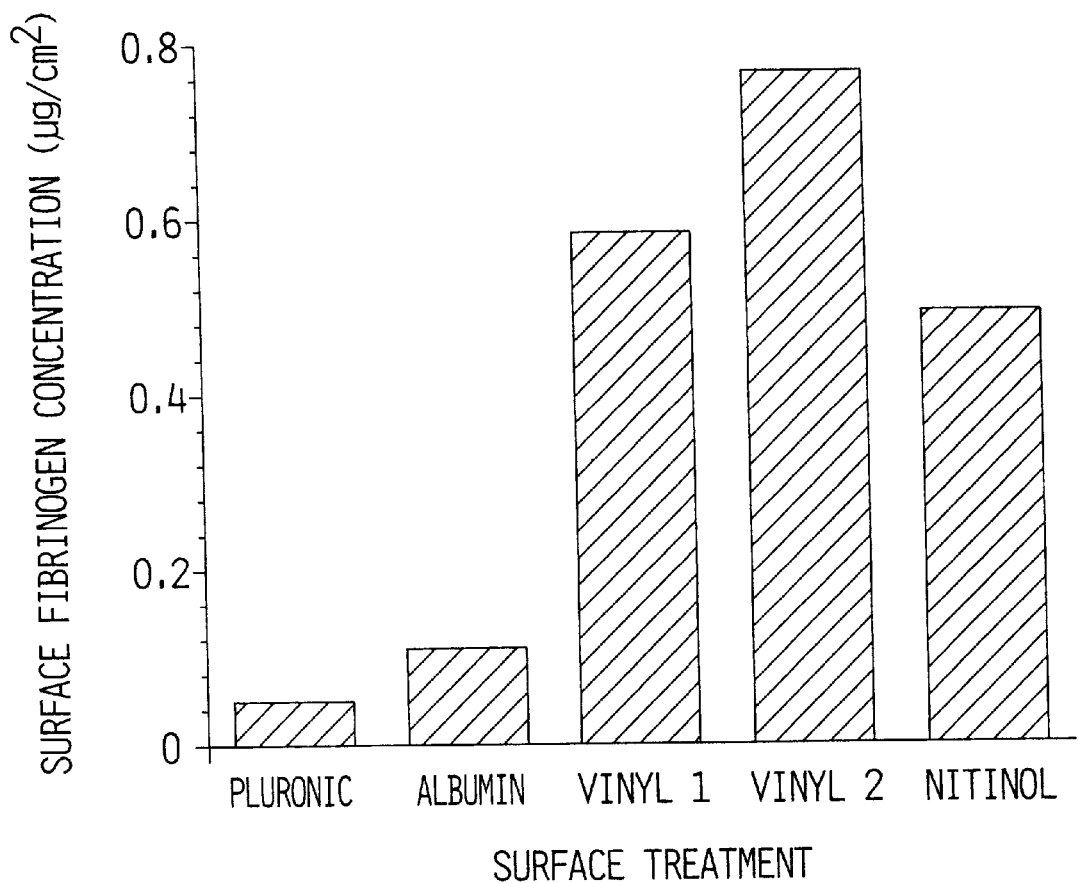
FIG_7

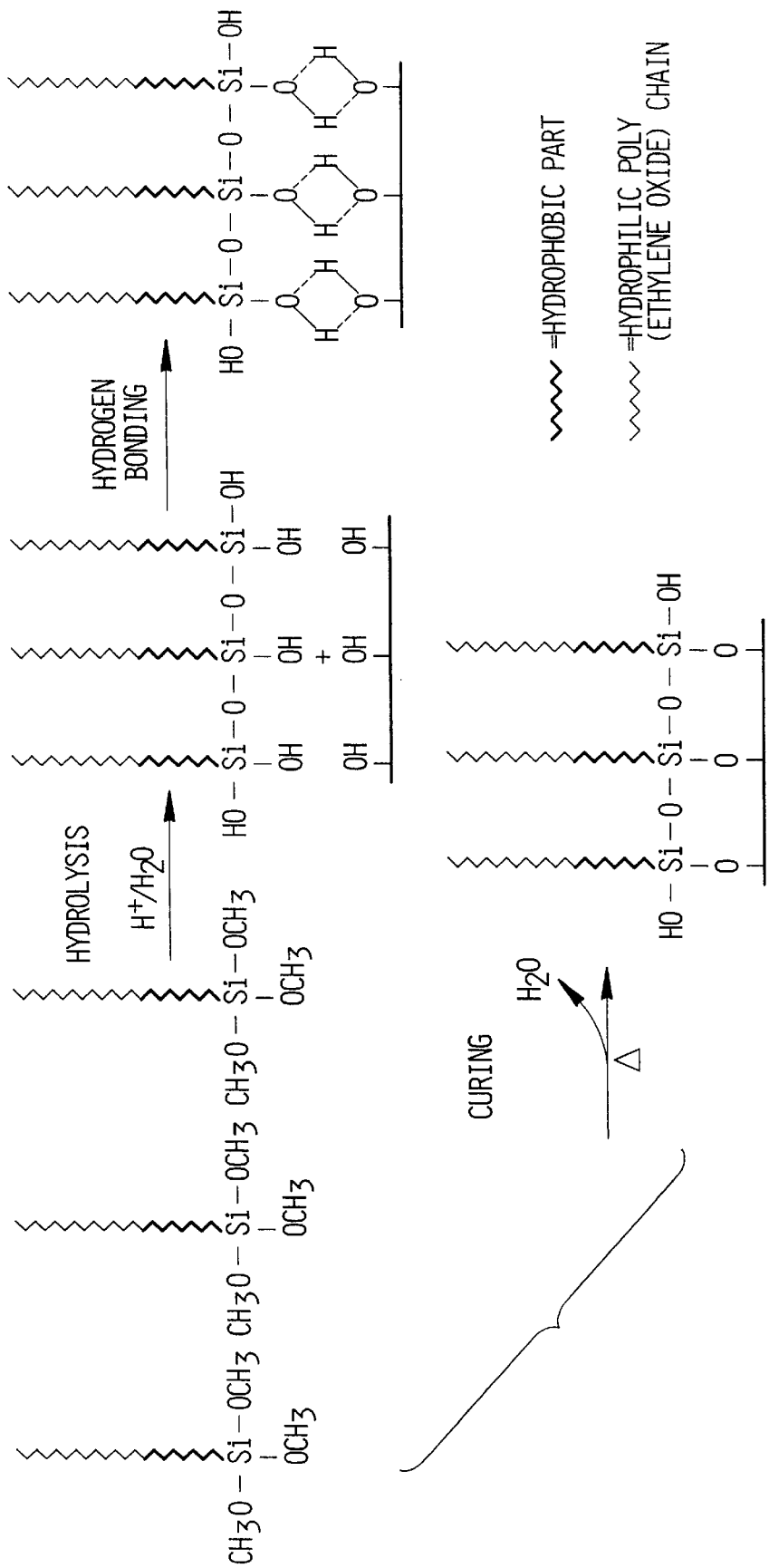

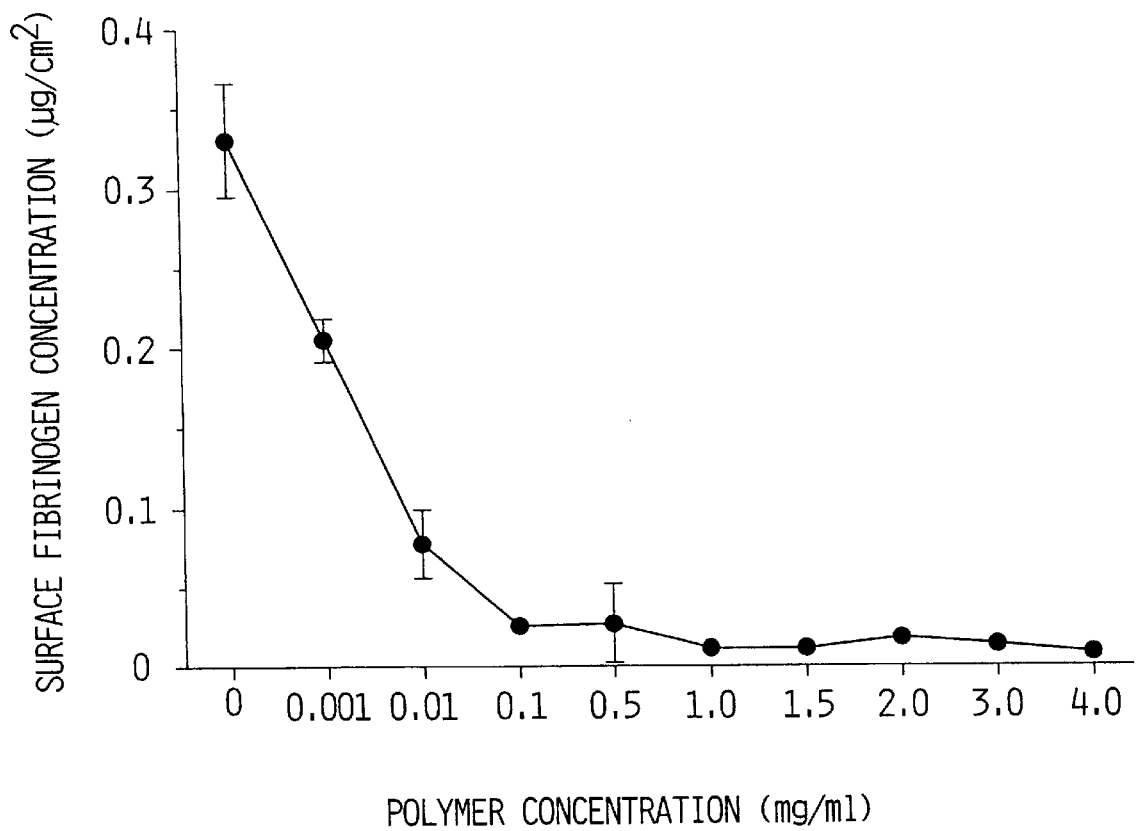
FIG_9

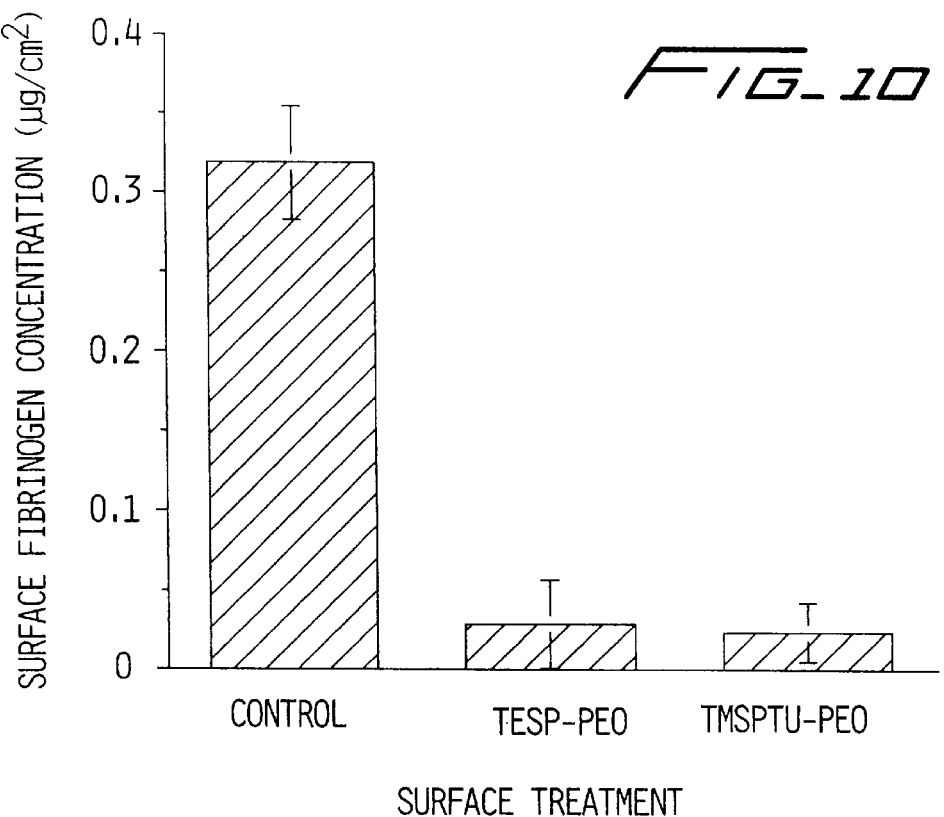
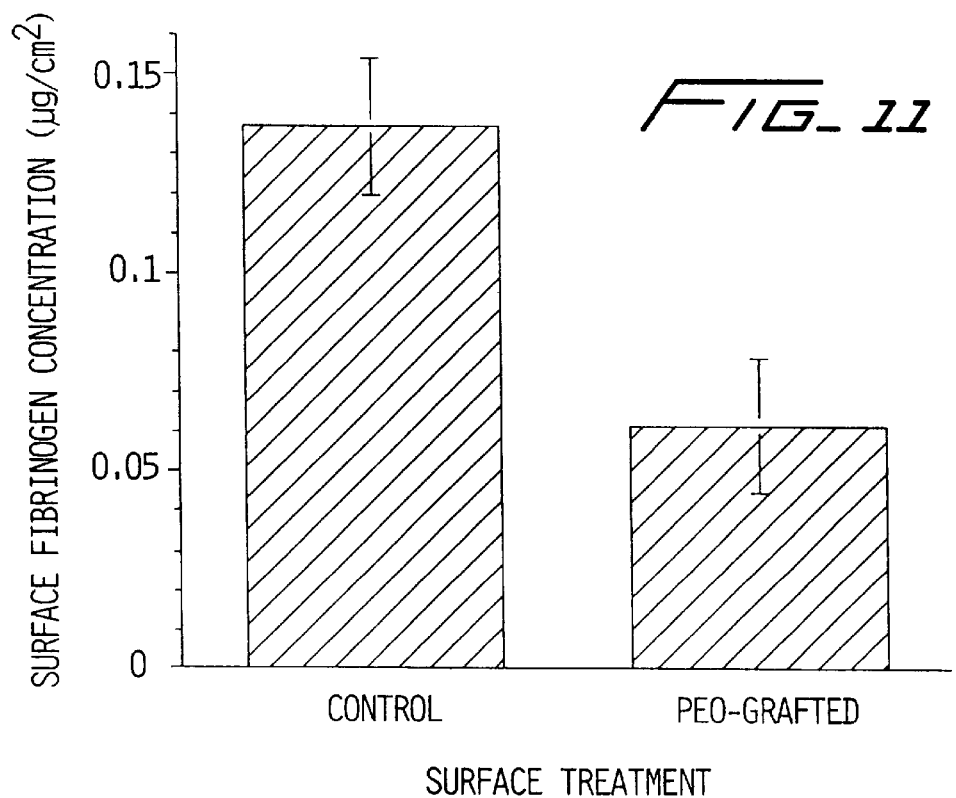

GRAFTING OF BIOCOMPATIBLE HYDROPHILIC POLYMERS ONTO INORGANIC AND METAL SURFACES

This application claims the benefit of U.S. Provisional Application Ser. No. 60/023,360, filed on Aug. 6, 1996.

The U.S. Government has a paid-up license in this invention and the right in limited circumstances to require the patent owner to license others on reasonable terms as provided for by the terms of Grant No. R01 HL 39081-09, awarded by NIH.

FIELD OF THE INVENTION

The present invention relates to methods for functionalizing inorganic and metal surfaces to render them more biocompatible. One method employs a vinyl silane coupling agent and covalently attaches poly(ethylene oxide) (PEO) or other hydrophilic polymers to vinylsilane functionalized surfaces by γ-irradiation. PEO is an excellent passivating agent for surfaces in contact with blood, which prevents the adsorption of proteins and adhesion of platelets. This method offers several advantages over other approaches in that no modification of the PEO is required. A second method employs silylated PEO or other silylated hydrophilic polymers for direct grafting of PEO (or hydrophilic polymer) to a surface. This process is simpler than other techniques in that it can be accomplished by dip coating.

REFERENCES

The following references are cited in the application as numbers in brackets ([ ]) at the relevant portions of the application.

1. Desai, N. et al., *J. Biomed. Mater. Res.* 25: 829–844, 1991.
2. Rollason, G. et al., *J. Biomed. Mater. Res.* 26: 675–693, 1992.
3. Llanos, G. R. et al., *J. Biomed. Mater. Res.* 27: 1383–1391, 1993.
4. Osterberg, E. et al., *Colloids Surfaces A. Physicochem. Eng. Aspects* 77: 159–169, 1993.
5. Maechling-Strasser, C. et al., *J. Biomed. Mater. Res.* 23: 1395–1410, 1989.
6. Lopez, G. P. et al., *J. Biomed. Mater. Res.* 26: 415–439, 1992.
7. Ishihara, K. et al., *J. Polym. Sci. Part A. Polym. Chem.* 30: 929–932, 1992.
8. Lee, J. et al., *J. Colloid Interface Sci.* 131: 252–266, 1989.
9. Tseng, Y.-C. et al., *J. Biomed. Mater. Res.* 26: 373–391, 1992.
10. Tseng, Y.-C. et al., *Biomaterials* 14: 392–400, 1993.
11. Tseng, Y.-C. et al. *J. Biomat. App.* 7: 233–249, 1993.
12. Amiji, M. et al. *Biomaterials* 682–692, 1992.
13. Amiji, M. et al., *J. Colloid Interface Sci* 155: 251–255, 1993.
14. Maechling-Strasser, C. et al., *J. Biomed. Mater. Res.* 23: 1385–1393, 1989.
15. Norman, M. E. et al., *J. Biomed. Mater. Res.* 27: 861–866, 1993.
16. Gingell, D. et al., *J. Biomed. Mater. Res.* 28: 491–503, 1994.
17. Amiji, M. et al., *J. Biomater. Sci. Polymer Edn.* 3: 375–388, 1992.
18. Yasuda, H. *Plasma Polymerization,* Academic Press: Orlando, Fla., 1985; pp. 432.
19. Kiaei, D. et al., *J. Biomed. Mater Res.* 26: 357–372, 1992.
20. Fujimoto, K. et al., *J. Biomed. Mater. Res.* 27: 1559–1567, 1993.
21. Tsubokawa, N. *Prog. Polym. Sci.* 17: 417–470, 1992.
22. Tsubokawa, N. et al., *J. Polym. Sci. Pt. A: Polym. Chem.* 30: 561–567, 1992.
23. Browne, T. et al., *J. App. Polym. Sci.* 44: 671–677, 1992.
24. Mathew, J. et al., *Polymer Journal* 24: 31–21, 1992.
25. Uchida, E. et al., *J. App. Polym. Sci.* 47: 417–424, 1993.
26. Wheals, B. B. *J. Chromatography* 107: 402–406, 1975.
27. Ferguson, G. S. et al., *Macromolecules* 26: 5870–5875, 1993.
28. Papirer, E. et al., *Chromatographia* 23: 639–647, 1987.
29. Pathmamanoharan, C. *Colloids Surfaces* 50: 1–6, 1990.
30. Lin, S. C. et al., *J. Biomed. Mater. Res.* 25: 791–795, 1991.
31 Sukenik, C. N. et al., *J. Biomed. Mater. Res.* 24: 1307–1323, 1990.
32. Vandenberg, E. et al., *J. Colloid Interface Sci.* 143: 327–335, 1991.
33. Dunkirk, S. G. et al., *J. Biomater. Appl.* 6: 131–156, 1991.
34. Tseng, Y.-C. et al., *Biomaterials* 16: 963–972, 1995
35. Kamath, K. et al., *J. Appl. Biomater.* 5: 163–173, 1994.
36. Kamath, K. et al., *Colloids Surfaces B: Bioint.* 2: 471–479, 1994.
37. Arkles, B. in *Silicon compounds: register and review 5th edition,* Anderson, R., Larson, G. L., and Smith, C., Ed.; Hüls America: Piscataway, N.J., 1991; Vol. 59–64.
38. Chvalovsky, V. in *Carbon-functional organosilicon compounds,* Chvalovsky, V., and Bellama, J., Ed.; Plenum Press: New York, 1984; Vol. 1–33.
39. Silberzan, P. et al., *Langmuir* 7: 1647–1651, 1991.
40. Ishida, H. et al., *J. Polym. Sci.: Polym. Phys. Ed.* 18: 1931–1943, 1980.
41. Plueddemann, E. *Silane coupling agents, second edition,* Plenum Press: New York, 1991; pp. 253.
42. Wirth, M. J. et al., *Anal. Chem.* 65: 822–826, 1993.
43. Ruhe, J. et al., *Langmuir* 9: 2383–2388, 1993.
44. Sun, F., et al.: *Colloids and Surfaces A: Physicochemical and Engineering Aspects,* 93: 191–200, 1994.
45. Sun, F., et al.: *Langmuir,* 9: 3200–3207, 1993.
46. Sun, F., et al.: *Macromolecules,* 27: 3053–3062, 1994.
47. Sun, F., et al.: *J. Vac, Sci. Technol.,* 12: 2499–2056, 1994.
48. Sun, F., et al.: *J. Am. Chem. Soc.,* 118: 1856–1866, 1996.
49. Topchiyeva, I. N., et al.: *Polymeric Sciences U.S.S.R.,* 32: 833–851, 1990.
50. Harris, J. M., et al.: *Journal of Polymer Science: Polymer Chemistry Edition,* 22: 341–352, 1984.
51. Zalipsky, S., et al.: *Eur. Polym. J.,* 19: 1177–1183, 1983.
52. Mutter, M., et al.: *Tetrahedron Letters,* 31: 2839–2842, 1978.
53. Bailey, D., et al.: *J. Macromol. Sci.-Chem.,* A12: 661–699, 1978.
54. Nagasaki, Y., et al. *Trends in polymer science,* 4: 59–64, 1996.

BACKGROUND OF THE INVENTION

When blood or biological fluids contact polymeric biomaterials, several processes occur including adsorption of plasma proteins, platelet adhesion and activation, and activation of the immune complement and coagulation pathways. The ultimate consequences of these processes are fouling and failure of the device and serious clinical complications. Modification of the biomaterial surface with albumin, heparin, and water soluble synthetic polymers such as poly(ethylene oxide) (PEO) is known to decrease or prevent these complications [1–13]. Surface modification of biomaterials with those surface-passivating molecules, however, has been rather difficult, since most of the biomaterials do not have any chemically active functional groups on their surfaces.

With respect to modifying surfaces with surface-passivating polymer molecules such as albumin and PEO, the simplest method is physical adsorption [5,8,14–16]. To utilize this method a hydrophobic surface, such as polypropylene or dimethyldichlorosilane (DDS)-glass, is exposed to an aqueous solution of albumin or PEO. Polymer molecules spontaneously adsorb to the surface due to the hydrophobic interaction. There is no chemical reaction between the polymer and surface, just physical interaction. The polymer layer is therefore not permanently bound to the surface, and generally can be removed with appropriate washing. This method is often ineffective for long-term prevention of protein adsorption and platelet adhesion, as other molecules or cells with a greater affinity for the surface may displace the physically adsorbed polymer. Furthermore, it has been suggested that drying of the surface may result in a heterogeneous polymer layer due to polymer molecules migrating with the receding water during the drying process. Drying and rehydration may also result in removal of the adsorbed polymer molecules from the surface. The surface concentration of the adsorbed albumin on DDS-glass was reduced by more than 15% by simple drying and rehydration [17]. Simple adsorption is therefore not appropriate for permanent applications of the modified surface.

For the covalent grafting of the surface-passivating molecules, the biomaterial surfaces have been premodified by various methods such as simple polymer adsorption, chemical surface-polymer coupling, and graft polymerization [1–8]. Previous approaches to permanently graft hydrophilic polymers to surfaces fall into two categories: graft polymerization and graft coupling. In graft polymerization, polymer chains are synthesized from the reactive surface. Alternatively, graft coupling binds polymer molecules to the surface through chemical reactions. Plasma polymerization and graft polymerization are the methods commonly employed in the former category, while various chemical methods comprise the latter approach.

Plasma polymerization, also known as glow discharge polymerization, is a method of polymerizing monomers from the vapor phase at low pressure. It is commonly used to polymerize monomers onto surfaces, resulting in a highly crosslinked polymer layer [18]. These highly cross-linked polymer layers are generally unable to prevent platelet adhesion on surfaces [6,19,20]. Rather, single chains of grafted polymer are necessary to exert the surface passivating effects. Graft polymerization is another process by which polymers are synthesized directly onto a reactive surface. In this approach, the substrate to be grafted is placed in a solution of the monomer. Polymerization is initiated by exogenous energy sources such as UV light, heat, or γ-radiation, or by chemical initiators [21–25]. The polymerization reaction proceeds both in the bulk solution yielding free-floating polymer chains and from the reactive sites on the surface yielding grafted chains. The surface reactive groups may resemble the monomer, so that the surface is included into a growing polymer chain, or it may otherwise contain the initiator groups, so that the grafted polymer chain actually begins growing from the surface. Trichlorovinylsilane (TCVS) has been used to modify surfaces prior to graft polymerization [26]. Producing consistent grafted surfaces is difficult to achieve with the graft polymerization technique. Since the polymers are synthesized in situ, there is little if any control over the degree of polymerization and the polymer grafting efficiency (i.e., the number of grafted polymer chains per unit area of surface). Polydispersity in molecular weights of the grafted chains confounds surface characterization. Depending on the polymerization method crosslinking of polymer chains may occur, leading to a 3-dimensional network of grafted polymer on the surface, rather than a layer of grafted individual chains. As mentioned above, the surface passivating effects of surface bound polymers is attributable to free polymer chains, not crosslinked polymer gels.

Chemical methods to graft purified polymer chains to surfaces have also been widely used [1–4, 27–32]. These methods employ chemical reactions between polymer molecules and reactive sites on the surface. Chemical grafting therefore relies on the presence of complementary reactive groups on the polymer and the surface, necessitating a different specific approach to each system. To utilize a specific polymer, it must already have a suitable reactive group or must be modified to contain such a reactive group. Because of this limitation chemical methods are of limited utility for generalized application. Each polymer-surface system is essentially a completely new project to be optimized for polymer synthesis and grafting conditions. The chemical methods have been used for immobilizing enzymes on supports and grafting polymer chains to various surfaces. Recently, surfaces have been modified with prefunctionalized polymers which are activatable by UV light, heat, or γ radiation. The use of activatable polymers allow grafting of polymer chains to otherwise inert surfaces. Examples of such polymers and their utility in surface modifications to prevent protein adsorption and cell adhesion are in the literature [9–11,13,33]. γ-radiation has also been used to graft hydrophilic polymer chains to various solid polymeric surfaces. In our laboratory we have synthesized several polymers which are activated by γ-radiation [17,34–36]. When activated, the polymer chains react with the surface and form a chemically bound polymer layer. In this method the polymer molecules adsorb from solution to the substrate surface and are then activated with γ-radiation to permanently graft to the surface. This approach requires that the highly reactive intermediates be in close proximity to the surface so that the activated polymer chains react with the surface. If the reactive groups are oriented away from the surface, they may react with adjacent polymer chains or with solvent water molecules. This results in very low grafting efficiency.

While hydrophilic polymer chains can be graft coupled to solid polymeric surfaces rather easily, their grafting to non-organic surfaces such as metals and glasses has been difficult. In contrast, the use of hydrophobic alkyl side chains to form ultrathin self-assembled polymeric films on solid surfaces has been done. [44–48]. Metals such as titanium and aluminum used in biomedical devices face the same blood compatibility problems as polymeric materials. The inorganic nature of metal surfaces makes them particularly difficult to graft with hydrophilic polymers such as PEO. Plasma polymerization has been used to graft metal surfaces with synthetic hydrophilic polymers [18]. As previously stated, however, the high degree of crosslinking inherent in plasma polymerization processes is not suitable for preparing protein and platelet resistant surfaces.

Recently, simple methods for the covalent grafting of surface-passivating molecules such as albumin and PEO have been developed [9–11]. The use of ultraviolet (UV) light, heat, or γ radiation for the covalent grafting of albumin or PEO to chemically inert surfaces such as polyethylene, polypropylene, polycarbonate, poly(vinyl chloride), and dimethyldichlorosilane (DDS)-coated glass was explored. In addition to albumin and PEO, poly(ethylene oxide)/poly (propylene oxide)/poly(ethylene oxide) (PEO/PPO/PEO) triblock copolymers were grafted using γ-irradiation [13].

Prior art methods have all rendered the modified surfaces resistant to protein adsorption and platelet adhesion. However, while these approaches are simple, highly effective, and can be applied to fully assembled devices in various shapes, they require introduction of activatable groups to the surface-passivating molecules. The preparation of activatable albumin or PEO requires rigorous synthesis and purification chemistry. In addition, these methods can only be used on polymeric biomaterials. Grafting of surface-passivating molecules to metal, glass, or ceramic surfaces is difficult with these methods.

Metallic materials are extensively used for construction of long term implantable cardiovascular devices such as prosthetic heart valves and stents. Several metallic materials enjoy wide acceptance due to their in vivo corrosion resistance. The electrochemical activity of blood makes corrosion resistance a major concern. As these materials are in contact with blood, it is desirable to improve their biocompatibility.

Titanium is used exclusively in prosthetic heart valves. Cobalt-chrome alloys, (such as STELLITE™ 21 and HAYNEST™ 25) tantalum, and nickel alloys are also used in prosthetic heart valves. These materials exhibit excellent corrosion resistance due to the high stability of the oxide layers on their surfaces. This oxide layer protects the deeper material from further oxidation. Clean titanium forms a tenacious titanium oxide layer, which is stable to saline solution, when exposed to air due to the high reactivity of the metal. Aluminum also reacts similarly, but the oxide layer which is formed is not stable to saline solution. The process of anodizing is required to stabilize aluminum oxide layers.

Blood contacting metallic materials are also found in cardiopulmonary surgical devices such as blood oxygenators. The heat exchangers which control blood temperature during surgery have very large surface areas for efficient heat transfer. They are made of anodized aluminum or stainless steel. Neither material is considered blood compatible, so the anticoagulant heparin is used to prevent blood clotting. Rendering the surfaces blood compatible by surface passivation may greatly reduce the doses of heparin required during such surgeries.

SUMMARY OF THE INVENTION

The present invention is based in part on the discovery of novel methods for preparing biocompatible surfaces. One approach is directed to grafting unmodified PEO or any other water-soluble polymers to the surfaces of metals and glasses.

In one aspect, the invention is directed to a method of grafting hydrophilic polymers to a surface of an article which includes the steps of:

(a) providing an article having a plurality of hydroxyl or oxide groups attached to a surface of said article;
(b) exposing said surface to a silane coupling agent to cause the silane coupling agent to form a silane layer that is covalently bound to the surface wherein the silane layer comprises a plurality of vinyl groups, wherein the silane coupling agent has the structure:

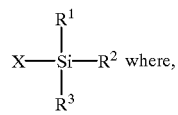

X is a non-hydrolyzable organic functional group terminating in a vinyl group, wherein at least one of said $R^1$, $R^2$, and $R^3$ is a hydrolyzable group with the others being a non-hydrolyzable group; and
(c) exposing the silane layer to a hydrophilic polymer and causing the silane layer to react with the hydrophilic polymer to covalently bond to the silane layer.

This inventive graft coupling technique enables the grafting of any suitable hydrophilic polymers to surfaces regardless of the presence of chemical functional groups on the polymer molecules to be grafted. Therefore, any surface which can be coated with vinyl group containing silane coupling agents can be grafted with virtually any polymer molecules by simply exposing to γ-irradiation. The presence of vinyl groups or, other double-bond containing groups, on the surface as a monolayer ensures that the polymer molecules to be grafted will be in direct contact with double bonds which generate free radicals by γ-irradiation. This makes covalent grafting of hydrophilic polymers highly efficient. Furthermore, it is much more likely that each polymer molecule will have multiple bonds to the surface, since individual polymer molecules are known to adsorb through multiple binding sites. This results in more secure grafting.

In another aspect, the invention is directed to a method of grafting hydrophilic polymers to a surface of an article includes the steps of:

(a) providing an article having a plurality of hydroxyl or oxide groups attached to a surface of said article;
(b) exposing said surface to a silanated hydrophilic polymer that has the structure:

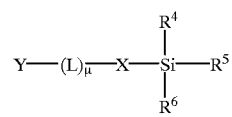

wherein at least one of said $R^4$, $R^5$, and $R^6$ is a hydrolyzable group each containing 1 to 6 carbon atoms, with the other(s) being nonhydrolyzable alkyl groups each containing 1 to 4 carbons, X is selected from an alkyl group, aryl group that is unsubstitued or substituted by one or more $C_{1-20}$ alkyl groups, Y is a hydrophilic polymer, such as, for example, poly(ethylene oxide) (PEO), poly(vinyl pyrrolidone) (PVP), poly(methacrylic acid) (PMA), poly(acrylic acid) (PAA), poly(hydroxyethylmethacrylate) (PHEMA), poly(vinyl alcohol) (PVA), or a natural polymer such as dextran. PEO is preferred. Hydrophilic polymers are soluble in an aqueous solution and maintain their flexible structures in aqueous environment. Preferably for the hydrophilic polymer, the number of monomer units can be as large as 10,000 or higher (i.e., the molecular weight of hydrophilic polymers can be as large as multi-million daltons). Preferred hydrophilic polymers for surface grafting have degrees of polymerization of from 1 to 2,000, preferably 1 to 500, and most preferably 1 to 150, and L is a linking moiety having one or more linking groups that is selected from amide (—C(O)NH—), ester (—C(O)O—), urea (—NHC(O)NH—), urethane (—OC(O)

NH—), ether (—O—), thioether (—S—), thiocarbamate (—OC(S)NH—), amine (—NH—), and mixture thereof provided that when L comprises more than one linking group, each is separated from the next by —(CH$_2$)$_m$— wherein m is an integer from 1 to 20, preferably 4 to 12, A is equal to 0 or 1; and (c) hydrolyzing the silanated hydrophilic polymer to form a silane layer; and (d) curing the silane layer to cause the silane layer to be covalently bonded to the surface of the article.

With this latter technique, silylated or silanated hydrophilic polymer having a hydrophobic domain can be grafted directly onto a surface. Indeed, a uniform monlayer of biocompatible material hydrophilic polymer can be obtained by dip coating. The invention is also directed to articles such as medical devices having surfaces that have been modified by the inventive techniques.

BRIEF DESCRIPTION OF THE DRAWINGS

FIG. 1 is a schematic representation of the silanization reaction;

FIG. 2 is a schematic representation of the γ-radiation induced polymer grafting to the vinyl-modified surface;

FIG. 3 is a graph showing fibrinogen adsorption to albumin- or PLURONIC® F127-grafted glass treated with either dimethyldichlorosilane (DDS) or trichlorovinylsilane (TCVS);

FIG. 4 is a graph showing fibrinogen adsorption to PLURONIC® F127- and bovine serum albumin (BSA)- grafted glass treated with either DDS or TCVS;

FIG. 7 is a graph showing fibrinogen adsorption to nitinol wires grafted with either PLURONIC® F127 or bovine serum albumin (BSA);

FIG. 8 is a schematic representation of PEO grafting using silanated PEO;

FIG. 9 is a graph showing the effect of the polymer concentration on the prevention of fibrinogen adsorption;

FIG. 10 is a graph showing the surface fibrinogen concentration on control glass and glass surfaces grafted with either triethoxysilylpropyl methoxy-PEO (TESP-PEO) or trimethoxysilylpropyl-thioundecyl methoxy-PEO 1,6-dicarbamato-hexane (TMSPTU-PEO); and FIG. 11 is a graph showing the surface fibrinogen concentration on control stent and stent grafted with triethoxysilylpropyl methoxy-PEO.

DESCRIPTION OF PREFERRED EMBODIMENTS

Figure 5:
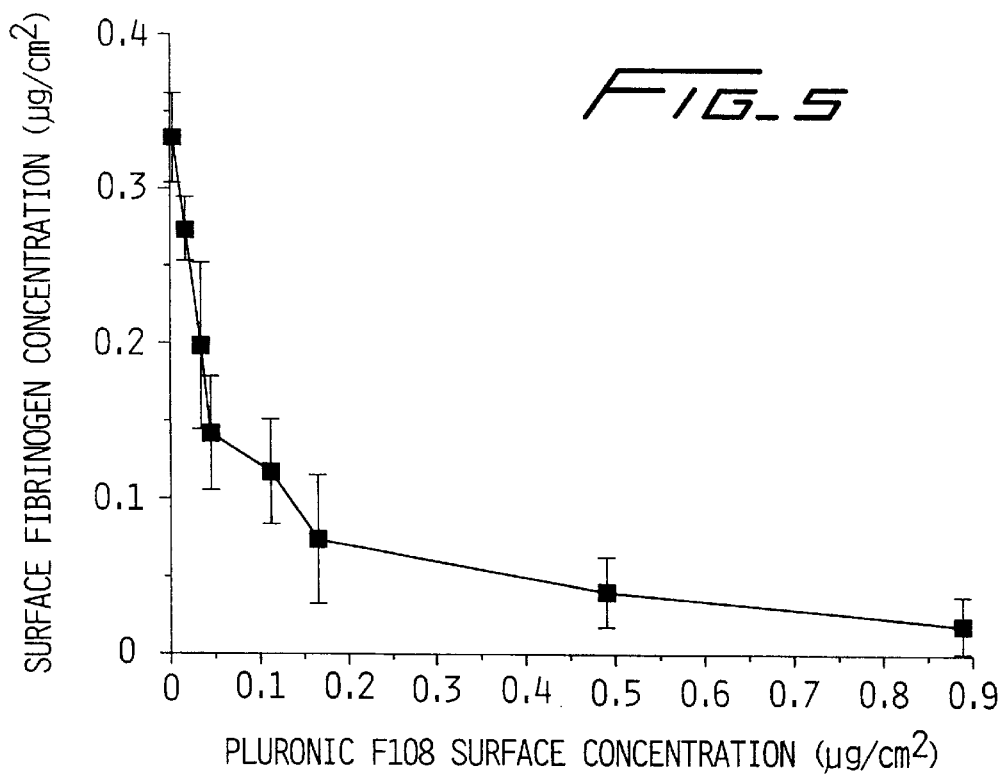
FIG. 5 is a graph showing fibrinogen adsorption to PLURONIC® F108-grafted TCVS glass.

I. Grafting Hydrophilic Polymers by γ-irradiation Through Vinylsilane Modification In one aspect, this invention relates to the introduction of vinyl groups to the surfaces of metals (with a suitable oxide and/or hydroxyl layer thereon), glasses, silica, clays, and other inorganic materials using silane coupling agent intermediaries which contain vinyl groups. Thereafter suitable hydrophilic polymers are covalently grafted to the silane coupling agent preferably by exposure to γ-irradiation or other source of radiation including, for example, X rays, and neutron or electron beam. However, prior to describing the invention in further detail, the following terms will be defined:

The term "silane coupling agent" refers to compounds of the general formula

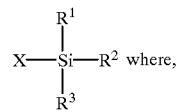

at least one of said R$^1$, R$^2$, and R$^3$ is a hydrolyzable group with the other(s) being a non-hydrolyzable group which is preferably any group that does not interfere with the surface silanization or polymer-surface coupling steps, and X is a non-hydrolyzable organic functional group terminating in a vinyl group, i.e., double-bonded carbon at the end of the chain. Preferred non-hydrolyzable groups include, for example, lower alkyls such as methyl and ethyl groups. Others include, for example, n-propyl, isopropyl, n-butyl, i-butyl, and t-butyl. Phenyl groups may also be applicable. Most preferably, each of said R$^1$, R$^2$, and R$^3$ is a hydrolyzable group. X preferably comprises a vinyl group and alkenyls, such as, for example, ethenyl, 3-propenyl, 4-buten-1-enyl, 6-hex-1-enyl, 8-oct-1-enyl groups. Preferred hydrolyzable groups include Cl atoms, alkoxy groups preferably having 1 to about 4 carbons, or mixtures thereof. Although hydrogen is a hydrolyzable group it is less stable than chloro- or alkoxysilanes. As further described herein, the hydrolyzable groups are displaced by water molecules during the initial curing process whereupon the silanol groups produced by displacement of the hydrolyzable groups react with the hydroxyl and/or oxide groups on the surface to be treated. Silane coupling agents having only 1 or 2 hydrolyzable groups will result in weaker bonding of the silane layer to the surface due to the presence of fewer bonds.

The most preferred silane coupling agents include, for example, trichlorovinylsilane (TCVS), trimethoxyvinylsilane (which is also known as vinyltrimethoxsilane), triethoxyvinylsilane (which is also known as vinyltriethoxysilane), vinyltriisopropoxysilane, vinyltri-t-butoxysilane, vinyltriphenoxysilane, vinyltriacetoxysilane, vinyltris (isobutoxy)silane, vinyltri(2-methoxyethoxy)silane, 8-oct-1-enyltrichlorosilane, 8-oct-1-enyltriethoxysilane, 8-oct-1-enyltrimethoxysilane, 6-hex-1-enyltrichlorosilane, 6-hexenyltriethoxysilane, and mixtures thereof.

Suitable silane coupling agents further include, for example, vinylmethyldiethoxysilane, vinylmethyldichlorosilane, vinylmethyldiacetoxysilane, vinylmethylbis(trimethylsiloxy)silane, vinylethyldichlorosilane, vinyldimethylethoxysilane, vinyldimethylchlorosilane, phenylvinyldiethoxysilane, phenylvinyldichlorosilane, phenylmethylvinylsilane, phenylmethylvinylchlorosilane, phenylmethylchlorosilane, 4-butenyldichloromethylsilane, and mixtures thereof.

Suitable silane coupling agents characterized by the presence of at least one hydrolyzable group and at least one non-hydrolyzable carbon-carbon double bond group, include, for example, vinyltris(methylethylketoximine) silane, vinylmethylbis(methylethylketoximine)silane, N-(3-trimethoxysilylpropyl)-N-methyl-N,N-diallylammonium chloride, 1,3,5,7-tetravinyltetramethylcyclotetrasiloxane, 1,1,3,3-tetravinyldimethyldisiloxane, (phenylethynyl) dimethylsilane, phenylallyldichlorosilane, 8-oct-1-enyldimethylchlorosilane, 3-methacryloxypropyltris (vinyldimethylsiloxy)silane, 3-methacryloxypropyltris (trimethylsiloxy)silane, 3-methacryloxypropyltris (methoxyethoxy)silane, 3-methacryloxypropyltrimethoxysilane, 3-methacryloxypropyltrichlorosilane, 3-methacryloxypropylmethyldimethoxysilane, 3-methacryloxypropylmethyldiethoxysilane, 3-methacryloxypropyldichlorosilane, 3-methacryloxypropyldimethylmethoxysilane, 3-methacryloxypropyldimethylethoxysilane, 3-methacryloxypropylbis(trimethylsiloxy)methylsilane, 3-methacryloxypropyltrimethoxysilane, 6-hex-1-enyldimethylchlorosilane, 1,3-divinyltetramethyldisiloxane, 1,3-divinyltetraethoxydisiloxane, 1,3-divinyl-1,3-dimethyl-1,3-dichlorodisiloxane, diphenylvinylethoxysilane, diphenylvinylchlorosilane, 1,3-bis(3-methacryloxypropyl)tetrakis(trimethylsiloxy)disiloxane, 1,3-bis(3-methacryloxypropyl)tetramethyldisiloxane, bis(dimethylamino)methylvinylsilane, 1,3-[(p-acryloxymethyl)phenethyl]tetramethyldisiloxane, allyltris(trimethoxysiloxy)silane, allyltrimethoxysilane, allyltriethoxysilane, allyltrichlorosilane, allylmethyldichlorosilane, allyldimethylsilane, allylmethylchlorosilane, 3-acryloxypropyltris(trimethoxysiloxy)silane, 3-acryloxypropyltrimethoxysilane, 3-acryloxypropyltrichlorosilane, 3-acryloxypropylmethyldimethoxysilane, 3-acryloxypropylmethyldichlorosilane, 3-acryloxypropylmethylbis(trimethylsiloxy)silane, 3-acryloxypropyldimethylmethoxysilane, N-(3-acryloxy-2-hydroxypropyl)-3-aminopropyltriethoxysilane, 1,3,5,7-tetramethyl-1,3,5,7-tetravinylcyclotetrasilazane, 3-(N-styrylmethyl-2-aminoethylamino)propyltrimethoxysilane hydrochloride, 1,3-divinyltetramethyldisilazane, 1,3-divinyl-1,3-diphenyl-1,3-dimethyldisilazane, bis(diethylamino)methylvinylsilane, and mixtures thereof. Additional silane coupling agents include vinyltriisopropenoxysilane, vinyltris(t-butylperoxy)silane, vinyltriisopropoxysilane, and vinyltriethoxysilane.

The silane coupling agent is preferably dissolved in a suitable solvent to form a solution which is placed in contact with the surface to be modified. While the choice of solvent employed depends, in part, on the silane coupling agent, preferred solvents include, for example, chloroform, methylene chloride, benzene, aqueous solutions of alcohols, such as, for example, methanol, ethanol, n-propanol, or isopropanol and mixtures thereof. The concentration of the silane coupling agent in solution preferably ranges from about 0.1% to 10% (v/v), more preferably about 1% to 5% (v/v), and most preferably about 3% (v/v). For silane coupling agents in which the hydrolyzable groups comprise a Cl atom, preferred solvents include organic solvent such as chloroform or methylene chloride. For alkoxysilanes, such as vinyltrimethoxysilane, for example, a preferred solvent is an aqueous alcohol solution. Preferably, the concentration range is about 0.1% to 10% (v/v) silane in a solvent of 90% to 95% (v/v) ethanol, more preferably about of 1% to 5% (v/v), and most preferably about 3% (v/v). The preferred application time ranges from about 0.5 hour to 6 hours, more preferably about 1 hour to 4 hours, and most preferably about 3 hours at ambient temperatures.

The term "hydrophilic polymer" refers to any suitable polymer which preferably reacts with the vinyl radicals. Preferred polymers include, for example, poly(ethylene oxide) (PEO), poly(hydroxyethyl methacrylate) (PHEMA), including amphophilic block copolymers which include PEO or PHEMA as the hydrophilic block, such as for example PEO-containing block copolymers, such as PLURONIC® (BASF Corp) PEO-PPO-PEO triblock copolymer, and mixtures thereof. Other suitable hydrophilic polymers include other hydrophilic polymers and amphiphilic copolymers of these, such as, for example, poly(vinyl alcohol) (PVA), polyvinylpyrrolidone (PVP), polyacrylamide, poly (acrylic acid), and mixtures thereof. Moreover, natural polymers including, for example, albumin, heparin, dextran, and mixtures thereof can also be employed.

A wide variety of PEO-PPO-PEO triblock copolymers are commercially available under the name of "PLURONIC®" (BASF Corp.) as exemplified by the list in Table 1. The types of PLURONIC® are classified according to the physical appearance. The liquid, paste, and solid PLURONICS® are designated as L, P, and F, respectively. The various PLURONICS® have different numbers of ethylene oxide (EO) and propylene oxide (PO) residues in their PEO-PPO-PEO triblock copolymers. Table 1 provides the numbers of EO and PO monomers in the triblock copolymers. The number of the monomer units of the PPO blocks typically range from 16 to 67, while that of PEO blocks typically range from 2 to 128.

TABLE 1

(Examples of PLURONIC ®s which can be grafted to a surface.)

| PLURO NIC® | EO | PO | EO | Mol. Wt. | PLURO NIC® | EO | PO | EO | Mol. Wt. |
|---|---|---|---|---|---|---|---|---|---|
| L121 | 6 | 67 | 6 | 4400 | L72 | 8 | 35 | 8 | 2750 |
| L122 | 13 | 67 | 13 | 5000 | P75 | 24 | 35 | 24 | 4150 |
| P123 | 21 | 67 | 21 | 5750 | F77 | 52 | 35 | 52 | 6600 |
| F127 | 98 | 67 | 98 | 12600 | | | | | |
| | | | | | L61 | 3 | 30 | 3 | 2000 |
| L101 | 7 | 54 | 7 | 3800 | L62 | 8 | 30 | 8 | 2500 |
| P103 | 20 | 54 | 20 | 4950 | L63 | 10 | 30 | 10 | 2650 |
| P104 | 31 | 54 | 31 | 5900 | L64 | 13 | 30 | 13 | 2900 |
| P105 | 38 | 54 | 38 | 6500 | P65 | 19 | 30 | 19 | 3400 |
| F108 | 128 | 54 | 128 | 14600 | F68 | 75 | 30 | 75 | 8400 |
| L92 | 10 | 47 | 10 | 3650 | L42 | 5 | 21 | 5 | 1630 |
| P94 | 21 | 47 | 21 | 4600 | L43 | 7 | 21 | 7 | 1850 |
| F98 | 122 | 47 | 122 | 13000 | L44 | 11 | 21 | 11 | 2200 |
| L81 | 6 | 39 | 6 | 2750 | L31 | 2 | 16 | 2 | 1100 |
| P84 | 22 | 39 | 22 | 4200 | L35 | 11 | 16 | 11 | 1900 |
| P85 | 27 | 39 | 27 | 4600 | F38 | 46 | 16 | 46 | 4700 |
| F87 | 62 | 39 | 62 | 7700 | | | | | |
| P88 | 97 | 39 | 97 | 11400 | | | | | |

L = liquid, P = paste, F = solid

The hydrophilic polymer is preferably dissolved in water to form a solution which is placed in contact for a sufficient amount of time with the surface that has been modified by the silane coupling agent. The hydrophilic polymer concentration and application time will vary depending on, among other things, the nature of the molecule. For example, triblock copolymers containing a hydrophobic segment, such as PLURONIC®, can be adsorbed to the surface very effectively even at low polymer concentrations. On the other hand, effective adsorption of hydrophilic homopolymers such as PEO requires high polymer concentrations as well as γ-irradiation in the presence of bulk PEO solution. The concentration of this solution preferably ranges from 0.01% to 50% (w/v), more preferably about 0.1% to 10% (w/v) and most preferably about 5%(w/v). The preferred application time ranges from about 0.25 hour to 4 hours, more preferably about 0.5 hour to 4 hours, and most preferably about 1 hour at ambient temperatures.

Protein adsorption to biomaterials grafted with PEO by this silanization process will preferably be less than about 0.25 $\mu g/cm^2$ (micrograms per square centimeter), more preferably less than about 0.10 $\mu g/cm^2$, and most preferably less than about 0.02 $\mu g/cm^2$. Plasma proteins such as, for example, fibrinogen and fibronectin preferably adsorb to materials grafted with PEO by this process at less than about 0.25 µg/cm$^2$, more preferably less than about 0.10 µg/cm$^2$ and most preferably less than about 0.02 µg/cm$^2$.

Mechanism of silanization and polymer grafting

The inventive graft coupling technique can be applied to improve the biocompatibility of devices having metallic or inorganic surfaces. It is particularly suited for biomedical devices or components which come into contact with blood. These devices include, for example, stents, angioplasty guidewires, pacemaker leads, and heart valves (which generally have metal components but are not totally metal). Non-biomedical applications include, for example, the coating of glass and stainless steel containers used for protein solutions to prevent costly product loss during pharmaceutical processing and packaging.

Although the invention is not limited by any particular theory, the inventive grafting technique will be illustrated with TCVS as the silane coupling agent and PEO as the hydrophilic polymer. The TCVS coating process is described schematically in FIG. 1. First, TCVS molecules are hydrolyzed by water adsorbed on the substrate surface yielding silanetriols. The silanetriol molecules then interact with each other and the hydroxyl- or oxide-rich surface by hydrogen bonding [37]. Finally, when dried and allowed to cure, the silanes and the surface condense forming a covalently bound silane layer. "Curing" refers to the formation of the covalent bonds between the silane molecules and the substrate surface [38,39].

The proposed mechanism of γ-induced grafting on the vinyl surface is similar to that of free radical polymerization. First, a vinyl group is ionized by absorption of γ photons, leaving surface bound free radicals. The radical species then attacks the adsorbed polymer molecule, forming a new covalent bond between the surface and the polymer. This mechanism of γ-induced grafting of a PLURONIC® molecule onto a TCVS surface is schematically described in FIG. 2. The long chains represent PEO blocks in the PLURONIC® molecule. The mechanism is similar for grafting of any other adsorbed molecule to the surface.

Stability of silanized surface

The stability of the surface-silane bond is of critical importance for coatings which are meant to be permanent. The most labile bond in the system is the ether bond between the silane and the surface (Si—O-surface), which is susceptible to cleavage by water. It has been shown that silanes with three hydrolyzable groups (e.g., the chloro substituents in TCVS, or alkoxy groups) form densely cross-linked layers, affording better stability than silanes with only one or two such groups. Also, the more hydrophobic the alkyl substituent, the more stable is the silane coating [40–42]. TCVS was shown to have good stability in epoxy-fiberglass systems in boiling water compared with other silanes. 8-Oct-1-enyltrichlorosilane, which is homologous with TCVS, but containing a saturated C$_6$ spacer between the Si atom and vinyl group should have even better water stability. It is known that alkyltrichlorosilanes, such as octadecyltrichlorosilane, form self assembled monolayers on glass where the C$_{18}$ tails associate due to the hydrophobic interaction to form a dense layer [43]. The C$_8$ silane is expected to exhibit the same behavior. It is expected that the stability of the C$_8$ layer will be at least as good as or surpass that of TCVS. 8-Oct-1-enyltrichlorosilane may therefore be a better choice for silanization.

The relative hydrolytic stabilities above were based on experiments conducted by immersing silane-coated glass fibers in water at 80° C. for up to 5000 hours. The materials were assayed by Fourier-Transform Infrared Spectroscopy (FTIR), a non-destructive technique, to determine the amount of silane remaining on the surface. The direct applicability of these data to surfaces meant for human biomedical applications is difficult to predict. Normal human body temperature is 37° C., which is significantly less than 80° C. Some of the samples in the study did not lose any silane from the surface for several hundred hours, followed by a relatively constant loss rate until very little silane remained. This effect is not expected when surfaces are subjected to a physiological medium. The long-term hydrolytic stability of silanized surfaces under realistic conditions, however, needs to be determined.

Another major factor to consider in silanized surface stability is the environmental pH. A shown herein, the pH of the solutions to which grafted surfaces will be subjected is important. The effect of pH on hydrolytic stability can be determined for specific applications.

EXPERIMENTAL

Method of polymer grafting on TCVS coated surfaces by irradiation

Glass substrates to be coated were first cleaned by soaking in chromic acid solution overnight, and rinsing in running deionized water. Metallic substrates were cleaned by vortexing in 1% sodium dodecylsulfate (SDS) solution for 5 min twice followed by rinsing in running deionized water. They were then dried in an oven at 60° C. overnight. The clean substrates were then immersed in a solution of 5% trichlorovinylsilane (TCVS, Aldrich Chemical Co., Milwaukee, Wis.) in chloroform (Mallinkrodt, analytical grade) for 3 h at room temperature. The silane-coated substrates were rinsed sequentially in fresh chloroform, absolute ethanol, and running deionized water. They are dried and cured at 60° C. overnight.

Polymers to be grafted were first dissolved in either phosphate buffered saline (PBS) for bovine serum albumin (BSA) or deionized distilled water (DDW) for synthetic polymers, such as PEO and PLURONICos, or natural polymers such as dextrans. The silanized substrates were then exposed to the polymer solution for 1 h for polymer adsorption to the surface. Samples were then either directly γ-irradiated as follows, or γ-irradiated after rinsing of the unabsorbed polymer molecules. The adsorbed polymer molecules were grafted to the substrates by exposure to γ-radiation from a $^{60}$Co source for a total dose ranging from 0.1 Mrad to 3.0 Mrad. The samples were then washed with 1% SDS overnight at room temperature to remove non-grafted polymer. They were then rinsed with running deionized water, and hydrated with PBS for at least 1 h prior to protein adsorption and platelet adhesion assays.

Analysis of protein adsorption and platelet adhesion to polymer grafted surfaces Protein adsorption assay:

Proteins to be adsorbed to polymer grafted test surfaces, either human fibrinogen or chicken egg lysozyme (Sigma Chemical Co., St. Louis, Mo.), were radiolabeled with $^{125}$I using the Enzymobead reagent (Bio-Rad). The radiolabeled protein is purified by gel filtration over a BioGel P6-DG column. Radiolabeled protein is mixed with native protein to produce the adsorption solution.

Sample surfaces were exposed to the protein solution for 1 h, then rinsed with PBS to remove non-adsorbed protein. The samples were then assayed on a γ scintillation counter (Beckman Gamma 5500B) to determine the amount of protein adsorbed to the surface. The raw data were divided by the sample surface area and protein specific activity to yield data in µg/cm$^2$ of adsorbed protein.

Platelet adhesion assay:

Platelet rich plasma (PRP) is separated from heparinized or citrated donor blood by centrifugation at 100 g for 5 minutes. Sample substrates were exposed to the PRP for 1 h at room temperature, then washed with PBS to remove non-adherent platelets. Adherent platelets were fixed with glutaraldehyde, labeled with rhodamine-phalloidin, and rinsed with PBS. The samples were examined by epifluorescence microscopy to determine the number and degree of activation of the adherent platelets.

Fibrinogen adsorption to TCVS glass grafted with either PLURONIC® F127 or bovine serum albumin (BSA)

FIG. 3 shows adsorption of fibrinogen (at the bulk concentration of 0.07 mg/ml) to DDS-glass and TCVS-glass which was grafted with either PLURONIC® F127 (PF127, EO/PO/EO=98/67/98) or BSA. Samples were exposed to 0.36 Mrad of γ radiation in the presence of bulk polymer solution at the concentration of 1.0 μg/ml, then washed with 1% SDS overnight at room temperature to remove non-covalently grafted molecules. For this graph, "PLURONIC®" and "albumin" represent PLURONIC® F127-grafted and bovine serum albumin-grafted surfaces, control 1 is DDS- or TCVS-treated glass exposed to γ-radiation in the absence of polymer, and control 2 is the plain DDS- or TCVS-glass.

The control silanized surfaces, i.e., DDS-glass and TCVS glass, exhibited very similar fibrinogen adsorption of 0.40 and 0.35 $\mu g/cm^2$, respectively. When exposed to 0.36 Mrad of γ-radiation in the presence of PBS, the silanized surfaces showed a lesser extent of fibrinogen adsorption of 0.37 and 0.21 $\mu g/cm^2$, respectively. This is likely due to oxidation of the surface during irradiation with a corresponding increase in hydrophilicity. TCVS-glass grafted with either PF127 or BSA showed very low fibrinogen adsorption of 0.004 and 0.005 $\mu g/cm^2$, respectively. These values represent a reduction in fibrinogen adsorption of approximately 99% compared to the control surface. Fibrinogen adsorption to DDS-glass exposed to 0.36 Mrad γ radiation in the presence of PF127 was 0.33 $\mu g/cm^2$, very similar to the control DDS-glass irradiated in the presence of DDW. This indicates that PF127 was not covalently grafted to the DDS-glass.

FIG. 4 shows fibrinogen adsorption to PF127 and BSA grafted TCVS and DDS glass. Samples were grafted as above. Some samples were not irradiated, but BSA was allowed to physically adsorb to the surface while the grafted samples were being irradiated. The BSA treated samples were washed with SDS 1%, either at room temperature overnight or at 100° C. for 1 hour. The PF127 grafted samples were washed at 100° C. for 1 hour. The fibrinogen concentration in the adsorption solution was 0.10 μg/ml.

For this graph:
Albumin 1A:BSA-grafted, washed at room temperature overnight;
Albumin 1B:BSA-grafted, washed at 100° C. for 1 hour;
Albumin 2A:BSA-adsorbed, washed at room temperature overnight;
Albumin 2B:BSA-adsorbed, washed at 100° C. for 1 hour;
PLURONIC®:PLURONIC® F127-grafted, washed at 100° C. for 1 hour.
Control:Plain TCVS- or DDS-glass The control DDS- and TCVS-glass samples, which were not γ-irradiated, show fibrinogen adsorption of 0.37 and 0.38 $\mu g/cm^2$, respectively. The PF127 treated DDS- and TCVS-glass surfaces exhibited fibrinogen adsorption of 0.35 and 0.004 $\mu g/cm^2$. Grafted PF127 was effective at reducing fibrinogen adsorption to TCVS-glass by 99%, while on the DDS-glass fibrinogen adsorption was reduced by less than 8%. The BSA grafted surfaces were more complicated to analyze. The BSA grafted to DDS and TCVS all show very low fibrinogen adsorption. Even the samples which were washed with boiling SDS kept fibrinogen adsorption below 0.025 $\mu g/cm^2$. The physically adsorbed BSA proved very difficult to remove from both surfaces by SDS washing, however. DDS and TCVS adsorbed with BSA for 7 hours at room temperature, then exposed to boiling SDS 1% for 1 hour showed fibrinogen adsorption of 0.33 and 0.15 $\mu g/cm^2$, respectively, while the samples washed at room temperature overnight showed fibrinogen adsorption of 0.12 and 0.09 $\mu g/cm^2$, respectively. This indicates that some BSA remains on the surface despite the washing steps. Considering the grafted and adsorbed samples together it seems evident that the BSA is being efficiently grafted to the TCVS-glass surface.

Fibrinogen adsorption to PLURONIC® F108-grafted TCVS-glass

FIG. 5 shows fibrinogen adsorption to PLURONIC® F108 (PF108, EO/PO/EO=128/54/128)-grafted TCVS-glass. TCVS-glass tubing was grafted with PF108 by adsorbing with solutions of PF108 in DDW for 1 hour, rinsing with DDW, then exposing the samples to 0.36 Mrad of γ-radiation. The grafted samples were washed with 1% SDS overnight. The fibrinogen concentration in the adsorption solution was 0.07 μg/ml.

The data were plotted as fibrinogen adsorption versus surface concentration of PF108. 0 $\mu g/cm^2$ represents the γ-radiation control TCVS-glass sample. The untreated TCVS-glass control surface showed fibrinogen adsorption of 0.35 $\mu g/cm^2$. The profile shows that at a low PLURONIC® surface density of 0.02 $\mu g/cm^2$, the fibrinogen adsorption was similar to control values, at 0.28 $\mu g/cm^2$. As the PF108 surface density increased up to 0.16 $\mu g/cm^2$, fibrinogen adsorption steadily decreases to 0.07 $\mu g/cm^2$. As the PF108 surface concentration increases from 0.16 to 0.88 $\mu g/cm^2$, fibrinogen adsorption appeared to approach a minimum value of 0.02 $\mu g/cm^2$. This value represents a decrease of 94% from the untreated TCVS-glass. The same experiments using PF127 grafted TCVS-glass show a consistent 99% decrease in fibrinogen adsorption when the solution concentration was 1 μg/ml. Those experiments employed γ-irradiation in the presence of polymer solution, while the PF108 samples were γ-irradiated in the presence of water after rinsing away excess polymer solution. Grafting in the presence of polymer solution consistently provided greater decrease in protein adsorption than grafting in the presence of water. The PF127 and PF108 differ in the length of the middle PPO segment. PF127 has a PPO block 67 units in length, while PF108 has only 54. It is known that the PLURONIC® polymers adsorb to hydrophobic surfaces through this middle segment. Therefore, the PF127 with a longer hydrophobic segment has a higher affinity for the TCVS surface, and is therefore grafted in higher density than PF108 at similar solution concentrations.

Lysozyme adsorption to TCVS-glass grafted with PLURONIC® F127

Figure 6:
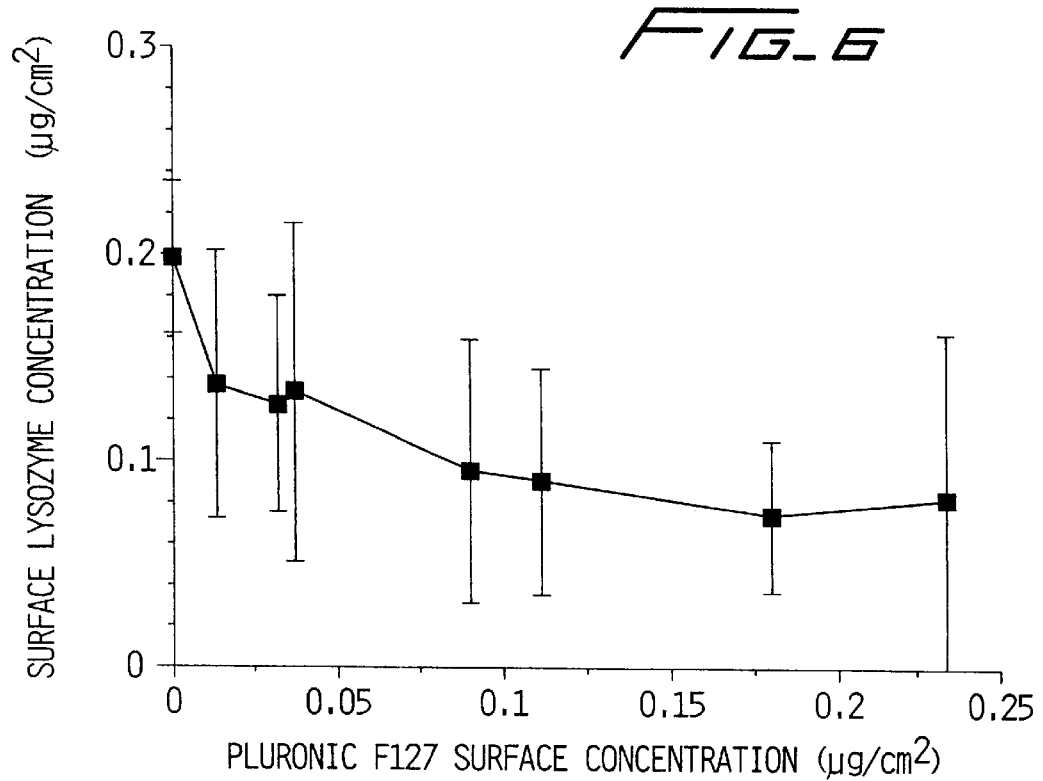
FIG. 6 is a graph showing lysozyme adsorption to PLURONIC® F127-grafted TCVS glass tubing.

FIG. 6 shows lysozyme adsorption to PLURONIC® F127-grafted TCVS-glass. Samples were adsorbed with PF127, rinsed with PBS, γ-irradiated for 0.36 Mrad, then washed with 1% SDS overnight. The lysozyme concentration used for adsorption study was 0.15 μg/ml.

The data are plotted as fibrinogen adsorption versus surface concentration of PLURONIC®. 0 $\mu g/cm^2$ represents the γ-radiation control TCVS-glass sample. Lysozyme adsorption to the control TCVS-glass, with and without exposure to 0.36 Mrad of g radiation in the presence of PBS was 0.19 and 0.27 $\mu g/cm^2$, respectively. As with fibrinogen adsorption to PF108 grafted TCVS-glass, lysozyme adsorption is similar to the control values at 0.14 $\mu g/cm^2$ when the surface PF127 concentration is 0.01 μg/cm². Lysozyme adsorption decreased steadily to 0.09 μg/cm² as the PF127 surface concentration increased up to 0.09 μg/cm². Lysozyme adsorption reached a minimum value of approximately 0.08 μg/cm² as PF127 adsorption increased up to 0.23 μg/cm². This value represents a decrease in lysozyme adsorption of 70% compared to untreated TCVS-glass. It appears that PF127 was relatively less effective at preventing lysozyme adsorption, whereas PF108 decreased fibrinogen adsorption by 94%. Lysozyme, however, is a much smaller molecule with a molecular weight of approximately 14,600 compared to fibrinogen, which has a molecular weight of approximately 340,000. Thus, lysozyme can reach places from which fibrinogen would be excluded.

Fibrinogen adsorption to Nitinol grafted with PLURONIC® F127 or bovine serum albumin FIG. 7 shows fibrinogen adsorption to nitinol wires grafted with either PLURONIC® F127 or BSA. The wires were grafted by adsorbing with the polymer, then grafting in the presence of bulk polymer solution. The concentration of BSA and PF127 were both 1 mg/ml. Grafted samples were washed by immersion in 1% SDS solution overnight. The fibrogen absorption is expressed in terms of apparent surface area because the nitinol wire has a rough surface and therefore the actual surface area is higher.

For this graph:
PLURONIC®: TCVS-coated nitinol grafted with PLURONIC® F127;
Albumin:TCVS-coated nitinol grafted with BSA;
Vinyl 1:TCVS-coated nitinol irradiated in the presence of water;
Vinyl 2:TCVS-coated nitinol without any irradiation;
Nitinol™: untreated nitinol control.
(Nitinol™ is a nickel-titanium alloy available from Raychem Corp., Menlo Park, Calif.)

Fibrinogen adsorption to the untreated nitinol wires was 0.50 μg/cm². The TCVS coated nitinol, with and without exposure to 0.36 Mrad γ radiation, exhibited fibrinogen adsorption of 0.59 and 0.77 μg/cm², respectively. PF127 and BSA grafting of the TCVS-coated wires reduced fibrinogen adsorption to 0.06 μg/cm² and 0.12 μg/cm², respectively. The reduction of fibrinogen adsorption to the nitinol wires by the grafted PF127 or BSA was similar to that observed with TCVS-glass. The process of silanization as well as γ-radiation induced polymer grafting were as efficient on nitinol as on glass surfaces. The calculation of the surface area of the fine nitinol wires may be imprecise, as the measurement of the wire diameter was difficult. The relative values in the fibrinogen adsorption, however, were still highly significant. PF127 and BSA reduced fibrinogen adsorption by 90% and 80%, respectively, compared to the untreated nitinol, and by 93% and 87% respectively, compared to the silanized nitinol.

Platelet adhesion to nitinol wires grafted with PLURONIC® F108 and PEO

Platelet-rich-plasma (PRP) was exposed to untreated nitinol, TCVS-coated nitinol, and TCVS-coated nitinol grafted with PF108 or PEO (MW=5000). PF108 and PEO were grafted by adsorbing for 1 h to the TCVS-coated surface, then washing with DDW, and γ-irradiating in the presence of DDW. In another process, nitinol wires were adsorbed with either PF108 or PEO for 1 h and γ-irradiated in the presence of bulk polymer solution. PF108 was used at a concentration of 1.0 mg/ml, while PEO was 10 mg/ml.

Untreated nitinol surfaces showed a nearly complete coverage of fully spread, activated platelets on the surface. There were several large aggregates dispersed throughout the surface. The TCVS-coated nitinol was also nearly completely covered with activated platelets. It showed more large aggregates than the untreated nitinol. Nitinol grafted with PF108 by adsorption, washing, then grafting in DDW showed much less platelet adhesion than either of the control surfaces. When viewed at 40× magnification, there were several viewing fields with no adherent platelets. Places where the platelets were present showed mostly contact adherent platelets and few, if any, fully activated ones. Wires with PF108 grafted in bulk polymer solution showed very much the same platelet response as the wires with PF108 grafted in DDW. Nitinol wires grafted with PEO by adsorbing, washing, and irradiating in the presence of DDW showed platelet adhesion intermediate between the control and PF108-grafted samples. There were several small aggregates, many fully activated platelets, and many contact-adherent platelets on the surface. The extent of coverage was less than the control, however, with space free of platelets separating the covered areas. PEO grafted by γ-irradiation in the presence of bulk polymer solution showed a varied response. Some areas were nearly free of platelets, exhibiting only spotty contact adherence, while other areas had aggregates of activated platelets. Yet, these activated aggregates were separated by platelet free areas. It appears that the most preferred surface treatment to prevent platelet adhesion and activation was grafting with PF108. The washing step after adsorption of PLURONIC® PF108 did not appear to influence the result.

II. Grafting Silylated Hydrophilic Polymers Containing a Hydrophobic Domain

In another aspect of the invention, silylated or silanated hydrophilic polymers having a hydrophobic domain is grafted directly to an inorganic or metal surface. A feature of this technique is that it can be accomplished by dip coating to form a uniform monolayer of biocompatible hydrophilic polymer such as PEO. Prior to describing this aspect of the invention, the following terms will be defined:

The term "silylated or silanated hydrophilic polymer" refers to compounds of the general formula

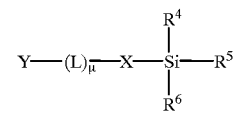

wherein at least one of said $R^4$, $R^5$, and $R^6$ is a hydrolyzable group containing 1 to 6 carbons, preferably 1 or 2 carbons, with the other(s) being nonhydrolyzable alkyl groups each containing 1 to 4 carbons, preferably 1 or 2 carbons. Most preferably, each of $R^4$, $R^5$, and $R^6$ is a hydrolyzable group. Preferred hydrolyzable groups include, for example, alkoxides —$OR^7$ where $R^7$ is an alkyl with 1 to 6 carbons, preferably $R^7$ is —$CH_3$ and halides such as Br, Cl and I. X is an anchoring moiety which connects L (when μ is equal to 1) to the silane coupling moiety, —Si($R^4R^5R^6$). X preferably comprises an aliphatic group (straight chain, branched or cylic), or an aromatic group which may be unsubstitued or substituted by one or more $C_{1-20}$ alkyl groups. The aliphatic group preferably has 1–15 carbons, more preferably 1–10 carbons. Most preferably, the aliphatic groups comprise —$(CH_2)_p$—, wherein p is from 1 to 8. Preferred aromatic groups have 5 or 6 carbons and are unsubstituted. μ is 0 or 1, preferably 1. L is a moiety having one or more linking groups that is selected from amide (—C(O)NH—), ester (—C(O)O—), urea (—NHC(O)NH—), urethane (—OC(O)NH—), ether (—O—), thioether (—S—), thiocarbamate (—OC(S)NH—), amine (—NH—), and mixture thereof provided that when L comprises more than one linking group, each is separated from the next by —$(CH_2)_m$— wherein m is an integer from 1 to 20, preferably 6 to 12. L may also comprise hydrophobic polymers such as, for example, poly(propylene oxide) (PPO), dicarboxy terminated poly(styrene), hydroxyl functionalized polybutadiene, polycaprolactone diol, and bis(3-aminopropyl) terminated polytetrahydrofuran. The precursor of X should have a functional group which reacts and bonds to suitably functionalized L. Specifically, one end of X is connected to the silane moiety through C—Si bond, and the other end is covalently bonded to L through a reaction with a functional group on the precursor X'. Preferred functional groups on X' include, for example, hydroxyl (—OH), mercapto (—SH), isocyanate (NCO), amine ($NH_2$), thiocyanate (NCS), carboxylic acid (COOH), aldehyde (CHO), and halides (Cl, Br, I); more preferably hydroxyl, mercapto, isocyanate, amine and halide; most preferably amine, mercapto, and isocyanate. Finally, Y is any biocompatible hydrophilic polymer (i.e., hydrophilic group or chain) including, for example, poly(ethylene oxide) (PEO), poly(vinyl pyrrolidone) (PVP), poly(methacrylic acid) (PMA), poly(acrylic acid) (PAA), poly(hydroxyethylmethacrylate) (PHEMA), poly(vinyl alcohol) (PVA), or a natural polymer such as dextran. Hydrophilic polymers are soluble in an aqueous solution and maintain their flexible structures in aqueous environment. The structures of Y for PVP, PHEMA, PVA, dextran, PAA, and PMA are as follows:

a) PVP

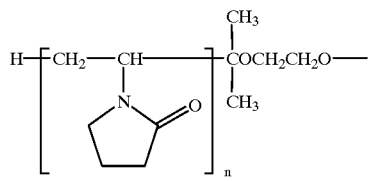

b) PHEMA

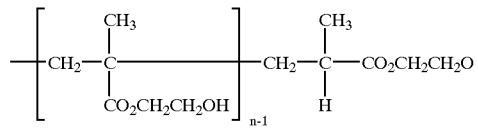

c) PVA

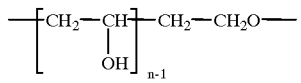

d) Dextran

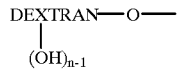

e) PAA

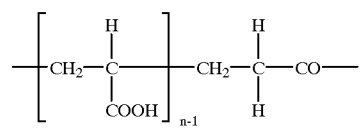

f) PMA

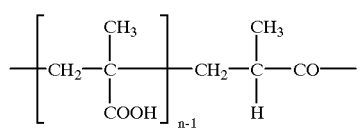

The number of monomer units can be as large as 10,000 or higher (i.e., the molecular weight of hydrophilic polymers can be as large as multi-million daltons). Preferred hydrophilic polymers for surface grafting have degrees of polymerization ranging from about 1 to 2,000, preferably about 1 to 500, and most preferably about 1 to 150. The hydrophilic polymers can be protected by being derivatized with a suitable terminal substituent. For example, in the case of PEO, the PEO chain may have a terminal alkoxyl group preferably having 1–3 carbons. For instance, methoxy-PEO, $CH_3O$—$(CH_2CH_2O)_n$— is a preferred embodiment for Y. Although Y may be any suitable biocompatible hydrophilic polymer (i.e., chain). the grafting of silanated hydrophilic polymers will be illustrated with silanated PEO.

Commercially available silane coupling agents X'—Si($R^4R^3R^6$) (where X' is the fuctionalized precursor of X) for the preparation of silanated PEOs include, for example, 4-aminobutyltriethoxysilane, (aminoethylaminomethyl) phenyltrimethoxysilane, aminobutyldimethyl methoxysilane, N-(2-aminoethyl)-3-aminopropylmethyldimethoxysilane, N-(2-aminoethyl)-3-aminopropyltrimethoxysilane, N-(6-aminohexyl) aminopropyltrimethoxysilane, 3-aminopropyldimethylethoxysilane, 3-aminopropylmethyldiethoxysilane, 3-aminopropyltriethoxysilane, 3-aminopropyltrimethoxysilane, (mercaptomethyl) dimethylethoxysilane, (mercaptomethyl) methyldiethoxysialne, 3-mercaptopropylmethyldimethoxysilane, 3-mercaptopropyltrimethoxysilane, 3-mercaptopropyltriethoxysilane, 3-isocyanatopropyltriethoxysilane, 8-bromooctyltrimethoxysilane, bromophenyltrimethoxysilane, 3-bromopropyltrimethoxysilane, 3-thiocyanatopropyltriethoxysilane. Most preferable coupling agents are 3-aminopropyltriethoxysilane, 3-aminopropyltrimethoxysilane, 3-mercaptopropyltrimethoxysilane, 3-mercaptopropyltriethoxysilane, and 3-isocyanatopropyltriethoxysilane.

When L comprises more than one linking group, L is a moiety that is derived from precursor L' which is a linear moiety having a functional group at each end, one that forms a bond to X and the other that bonds to the m-PEO. (m-PEO shall refer to $CH_3O$—$(CH_2CH_2O)_n$—$CH_2CH_2$— of the silylated or silanated PEO compounds.) L comprises a linear chain wherein the length can be varied through the connection of 1,ω-difunctional linear hydrocarbons. For example, L can be linked to X through an (1) amide, such as m-PEO—OC(O)$CH_2CH_2$C(O)—NH—$(CH_2)_{10}$C(O)NH$(CH_2)_3$Si($R^4R^5R^6$), (2) ester, such as m-PEO—OC(O)$CH_2CH_2$C(O)—NH—$(CH_2)_{10}$C(O)O$(CH_2)_3$Si($R^4R^5R^6$), (3) urea, such as m-PEO—OC(O)NH$(CH_2)_6$NHC(O)NH$(CH_2)_3$Si($R^4R^5R^6$), (4) urethane, such as m-PEO—OC(O)NH—$(CH_2)_6$ NHC(O)O$(CH_2)_3$Si($R^4R^5R^6$), (5) ether, such as m-PEO—OC(O)NH—$(CH_2)_6$NHC(O)O$(CH_2)_6$—O—$(CH_2)_3$Si($R^4R^5R^6$), (6) thioether, such as as m-PEO—OC(O)NH—$(CH_2)_6$NHC(O)O$(CH_2)_{11}$—S—$(CH_2)_3$Si($R^4R^5R^6$), (7) thiocarbamate, such as m-PEO—OC(O)NH—$(CH_2)_6$ NHC(O)O$(CH_2)_6$OC(S)NH$(CH_2)_3$Si($R^4R^5R^6$), and (8) amine, such as m-PEO—OC(O)NH—$(CH_2)_6$NHC(O)NH$(CH_2)_6$NH—$(CH_2)_3$Si($R^4R^5R^6$). Most preferred linkage groups are amide, urethane, urea, thioether, and thiocarbamate. They can form more stable bonds than ester in vivo. Amine and ether linkages are less preferred because of the possibilty of competitive reaction of hydrolyzable groups during the reaction.

m-PEO links to L or X (in the case where $\mu$ is 0) through (1) ether, such as m-PEO—O—$(CH_2)_3Si(R^4R^5R^6)$, (2) ester, such as m-PEO—OC(O)$CH_2CH_2C(O)$—NH—$(CH_2)_{10}C(O)O(CH_2)_3Si(R^4R^5R^6)$, (3) amide, such as m-PEO—OC(O)$CH_2CH_2C(O)$—NH—$(CH_2)_{10}C(O)NH(CH_2)_3Si(R^4R^5R^6)$, (4) urethane, such as m-PEO—OC(O)NH—$(CH_2)_6$ NHC(O)O$(CH_2)_3Si(R^4R^5R^6)$, (5) urea, such as m-PEO—OCH$_2$CH$_2$ NHC(O)NH—$(CH_2)_6$NHC(O)O $(CH_2)_3$ $Si(R^4R^5R^6)$, and (6) amine, such as m-PEO—OCH$_2$CH$_2$—NH—$(CH_2)_6$NHC(O)NH$(CH_2)_3Si(R^4R^5R^6)$. Most preferable linkages are urethane, ether, and amine, because they are stable in vivo.

L comprises one or more linking groups selected from (1) amide, such as m-PEO—OC(O)$CH_2CH_2C(O)$—NH—$(CH_2)_{10}C(O)NH(CH_2)_{10}C(O)NH(CH_2)_3Si(R^4R^5R^6)$, (2) ester, such as m-PEO—OC(O)$CH_2CH_2C(O)$—NH—$(CH_2)_{10}C(O)O(CH_2)_6$—O—C(O)NH$(CH_2)_3Si(R^4R^5R^6)$, (3) urethane, such as m-PEO—OC(O)NH—$(CH_2)_6$NHC(O)O$(CH_2)_{11}$—S—$(CH_2)_3Si(R^4R^5R^6)$, (4) urea, such as m-PEO—OC(O)NH—$(CH_2)_6$NHC(O)NH$(CH_2)_{12}$NHC(O)NH$(CH_2)_3Si(R^4R^5R^6)$, (5) ether, such as m-PEO—O$(CH_2)_3$O$(CH_2)_6$OC(O)NH$(CH_2)_3Si(R^4R^5R^6)$, (6) thioether, such as m-PEO—OC(O)NH—$(CH_2)_6$NHC(O)O$(CH_2)_{11}$—S—$(CH_2)_4$OC(O)NH$(CH_2)_3Si(R^4R^5R^6)$, and (7) amine, such as m-PEO—NH$(CH_2)_6$NH$(CH_2)_6$NHC(O)NH$(CH_2)_3Si(R^4R^5R^6)$, or mixtures thereof. Preferred linking groups are urethane, urea and ether because they are durable to hydrolysis in vivo.

When L comprises more than one linking group each is separated from the next by —$(CH_2)_m$— wherein m is from 1 to 20, preferably 1 to 12, more preferably 4 to 12. Preferred difunctional aliphatic (aryl or aromatic) chemicals which are commercially available for the preparation of L in a silanated PEO include, for example, 1,4-diisocyantobutane, 1,6-diisocyanatohexane, 1,4-diisocyanatobenzene, 1,8-diisocyanatooctane, 1,5-diisocyanato-2-methylpentane, 1,12-diisocyanatododecane, 10-undecen-1-ol, 5-hexen-1-ol, 9-decen-1-ol, 1,12-diaminododecane, 1,10-diaminodecane, 1,9-diaminononane, 1,8-diaminooctane, 1,7-diaminoheptane, 1,5-diaminopentane or mixtures thereof, most preferably 1,6-diisocyanatohexane, 1,8-diisocyanatooctane, 1,12-diisocyanatododecane, 10-undecen-1-ol, and 1,12-diaminododecane, poly(propylene oxide) (PPO), dicarboxy terminated poly(styrene), hydroxyl functionalized polybutadiene, polycaprolactone diol, and bis(3-aminopropyl) terminated polytetrahydrofuran or mixtures thereof.

Preferred silylated PEO coupling agents include, for example: (1) monomethoxy poly(ethylene glycol)(m-PEO) alkyl trialkoxysilanes such as 8-(m-PEO) octyl trimethoxy (or ethoxy) silane, 6-(m-PEO) hexyl trimethoxy(or ethoxy) silane and 4-(m-PEO) butyl trimethoxy(or ethoxy) silane; (2) trialkoxysilylalkyl m-PEO carbamates such as triethoxy (or methoxy) silylpropyl m-PEO carbamate; (3) trialkoxysilylalkylureidoalkyl m-PEO carbamates such as trimethoxy (or ethoxy) silylpropylureidohexyl(butyl, octyl or dodecyl) ureido m-PEO carbamate; (4) trialkoxysilylalkylthioalkyl m-PEO 1,ω-dicarbamatoalkanes such as trimethoxy (or ethoxy) silylpropylthioundecyl(butyl, pentyl, hexyl, heptyl, octyl or decyl) m-PEO 1,ω-dicarbamatohexane (butane, octane or dodecane); (5) trialkoxy silylalkylthioalkylm-PEOs such as trimethoxy(or ethoxy) silylthioundecyl (butyl, pentyl, hexyl, heptyl, octyl or decyl) m-PEO; (6) m-PEO trialkoxysilylalkylates such as m-PEO trimethoxy (or ethoxy) silylbutanoate (hexanoate, pentanoate, octanoate, decanoate or undecanoate); (7) trialkoxysilylalkyl m-PEO trimethoxy (or ethoxy) silylbutanoate (hexanoate, pentanoate, octanoate, decanoate or undecanoate); (8) trialkoxysilylalkyl m-PEO succinate (malate or glutarate); (9) trialkoxysilylalkyl m-PEO succinyl (maleyl or glutaryl) amides; and (10) trialkoxysilylalkylthio m-PEOs such as trimethoxy (or ethoxy)silylpropylthio m-PEO.

Structures and synthesis of some preferred silanated PEOs include:

(1) m-PEO alkyl trimethoxysilane,

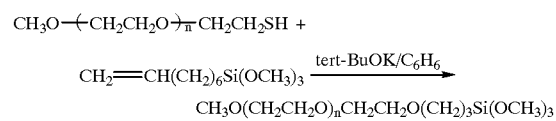

This reaction is further described in Topchiyeva, I. N. et al., [49] and Harris, J. M., et al., [50].

(2) trimethoxysilylalkyl m-PEO carbamate

A method of synthesizing triethoxysilylpropyl m-PEO carbamate is described herein.

(3) trimethoxysilylalkylureidoalkyl m-PEO carbamate,

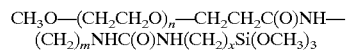

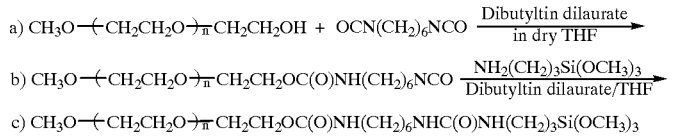

This reaction is further described in Topchiyeva, I. N. et al. [49] and Zalipsky, S. et al, [51].

(4) trimethoxysilylalkylthioalkyl m-PEO 1,ω-dicarbamatealkane

A method of synthesizing trimethoxysilylpropylthioundecyl m-PEO 1,6-dicarbamatohexane is described herein.

(5) trimethoxysilylalkylthioalky m-PEO,

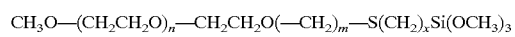

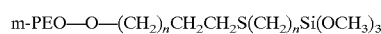

(I)

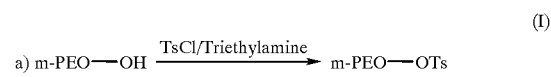

-continued b) $CH_2=CH(CH_2)_nOH \xrightarrow[\text{in Toluene}]{(CH_3)_3CO^-K^+} CH_2=CH(CH_2)_nO^-K^+$ (II)

c) (I) + (II) $\xrightarrow{\text{in Toluene}}$ m-PEO—O—$(CH_2)_nCH=CH_2 \xrightarrow{SH(CH_2)_3Si(OCH_3)_3}_{AIBN, 60° C.}$ m-PEO—O—$(CH_2)_nCH_2CH_2S(CH_2)_3Si(OCH_3)_3$ This reaction is further described in Topchiyeva, I. N. et al. [49], Harris, J. M. et al., [50], Mutter, M. et al., [52], Bailey, D., et al, [53], and Nagasaki, Y. et al., [54].

(6) m-PEO trimethoxysilylalkylate $CH_3O-(CH_2CH_2O)_n-CH_2CH_2OC(O)(CH_2)_nSi(OCH_3)_3$ $CH_3O(CH_2CH_2O)_nCH_2CH_2OH +$
$HOC(O)(CH_2)_nSi(OCH_3)_3 \xrightarrow{DCC/DMAP}$
$CH_3O-(CH_2CH_2O)-CH_2CH_2OC(O)(CH_2)_nSi(OCH_3)_3$ DCC : Dicyclohexyl carbodiimide
DMAP: Dimethylaminopyridine
(7) trimethoxysilylalkyl m-PEO succinyl(maleyl or glutaryl) amide, $CH_3O-(CH_2CH_2O)_n-$
$CH_2CH_2OC(O)(CH_2)_mC(O)NH(CH_2)_xSi(OCH_3)_3$

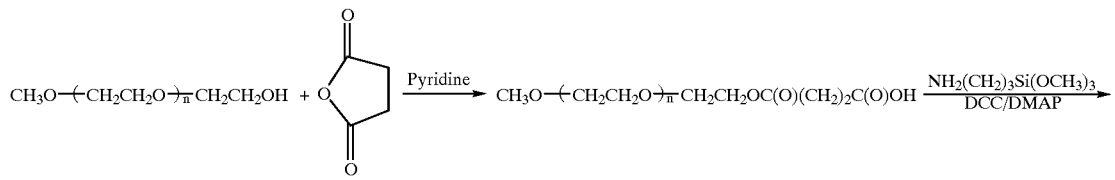

(8) trimethoxysilylalkylthio m-PEO, $CH_3O-(CH_2CH_2O)_n-CH_2CH_2S(CH_2)_mSi(OCH_3)_3$ $CH_3O-(CH_2CH_2O)_n-CH_2CH_2S(CH_2)_mSi(OCH_3)_3$ $CH_3O-(CH_2CH_2O)_n-CH_2CH_2SH +$ $CH_2=CH(CH_2)_6Si(OCH_3)_3 \xrightarrow[\text{in Toluene, 60° C.}]{AIBN}$ $CH_3O-(CH_2CH_2O)_n-CH_2CH_2S(CH_2)_8Si(OCH_3)_3$ This reaction is further described in Nagasaki, Y., et al, [54].

EXPERIMENTAL
Mechanism of polymer grafting

FIG. 8 is a schematic representation illustrating how PEO grafting occurs using silanated PEO. The hydrolyzable moieties (i.e., methoxy groups) of silanated PEO are hydrolyzed in aqueous solution by acid-catalysts. Such hydrolysis results in oligomerization of silanated PEO. Some available silanol groups from acid-catalyzed hydrolysis form hydrogen bonds with hydroxyl groups on the surface. Curing at an elevated temperature, preferably 40° C. and above, leads to dehydration at the surface and formation of covalent bonds between silanated PEO and the surface hydroxyl groups.

Preparation of representative silane PEOs containing hydrophobic domains.

1. Synthesis of triethoxysilylpropyl m-PEO carbamate (Formula I) via the following reaction:

$CH_3O(-CH_2CH_2-)_nOH + O=C=NCH_2CH_2Si(OCH_2CH_3)_3$

Dibutyltin Dilaurate $\rightarrow CH_3O-(CH_2CH_2-)_nOC(O)NHCH_2CH_2CH_2Si(OCH_2CH_3)_3$ (I)

Silylated PEO coupling agents which are directly applicable to the surface modification can be synthesized using 3-isocyanatopropyltriethoxy silane and PEOs with different molecular weights. Triethoxysilylpropyl PEO carbamate (Formula I) was prepared by the following procedure. Twenty w/v % PEO solution in tetrahydrofuran (THF) from Malinckcrodt Chemical (40 g of PEO in 200 ml of THF) was prepared in 1000 ml three-necked, round-bottomed-flask under dry nitrogen. 3-isocyanatopropyltriethoxy silane (IPTS) and dibutyltin dilaurate as a catalyst were added to the PEO solution. The molar ratios of IPTS and dibutyltin dilaurate to PEO were 2.5 and 0.1, respectively. After adding chemical reagents, the mixture was stirred continuously for 48h under dry nitrogen. After the reaction, the silylated PEO coupling agent was twice precipitated with hexane from THF, and dried in vacuo.

The reagent THF was purified by refluxing with lithium aluminum hydride (LiAlH$_4$; Aldrich) overnight and distilling from LiAlH$_4$ to remove water and impurities. Commercially available methoxy PEOs whose molecular weight were 5000 and 2000 (from Aldrich) were dried by azeotropic distillation in benzene overnight to remove adsorbed water, and benzene was distilled out under reduced pressure, IPTS was used without further purification.

2. Synthesis of trimethoxysilylproplthioundecyl m-PEO 1,6-dicarbamatohexane (Formula V) via the following reactions:

$CH_3O-(CH_2CH_2O)_n-H + OCN(CH_2)_6NCO \xrightarrow{\text{Dibutyltin dilaurate}}$ $CH_3O-(CH_2CH_2O)_{n-1}-CH_2CH_2-OC(O)NH(CH_2)_6NCO \xrightarrow[\text{Dibutyltin dilaurate}]{HO(CH_2)_9CH=CH_2/}$ -continued

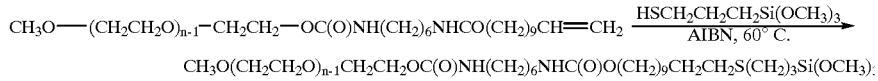

$$CH_3O(CH_2CH_2O)_{n-1}CH_2CH_2OC(O)NH(CH_2)_6NHC(O)O(CH_2)_9CH_2CH_2S(CH_2)_3Si(OCH_3)_3$$

Preparation of m-PEO—NCO (Formula II)

Forty grams of monomethoxy PEO 5,000 (Aldrich) was dissolved in 250 ml of benzene and adsorbed water was removed by azotropic distillation. A 500 ml three necked, round bottomed flask was charged with 5 times molar excess of 1,6-diisocyanatohexane (Adrich) to m-PEO and 150 ml of THF. Under nitrogen atmosphere, 10% m-PEO solution in THF and 0.5 ml of dibutyltin dilaurate were added dropwise to hexamethylene diisocyanate solution. Reaction mixture has been stirred magnetically for 16 hr at the room temperature. After the reaction, m-PEO—NCO was precipitated by using n-hexane, and dried overnight in a vacuum oven. THF was purified by refluxing with $LiAlH_4$ (Aldrich) overnight and distilling from $LiAlH_4$ to remove water and impurities.

Preparation of m-PEO 10-undecenyl dicarbamatohexane (Formula III)

Seven grams of m-PEO—NCO in 150 ml of THF was charged to a 250 ml round bottomed, three necked flask. 2.5 ml of 10-undecenol and 0.1 ml of dibutyltin dilaurate were added to the m-PEO—NCO solution, and reaction mixture was stirred overnight at the room temperature. After reaction, the product was precipitated with n-hexane, and purified further by recrystallization with ethanol.

Silylation of m-PEO 10-undecenyl dicarbamatohexane (m-PEO—HM—UN) (Formula IV)

Fifty ml of benzene containing 5g of m-PEO—HM—UN, 1.5 ml of 3-mercaptopropyl trimethoxy silane, and 0.041 g of AIBN were charged to a 250 ml round bottomed flask. Reaction mixture was degassed by using a mechanical pump, and purged with nitrogen gas. The temperature of reaction solution was adjusted to 60–65° C. using an oil bath, and kept for 1 day during magnetic stirring. The final product was precipitated by anhydrous diethylether, and extensively washed to remove AIBN and remaining 3-mercaptopropyl trimethoxy silane.

Representative methods of synthesizing silanated hydrophilic polymers other than silanated PEO.

a) Silanated PVP. PVP can be end-functionalized to introduce —OH groups using the method described by Sartore et al. "Low Molecular Weight End-Functionalized Poly (N-vinylpyrrolidinone) for the Modification of Polypeptide Aminogroups," *J. of Bioactive and Compatible Polymers,* 9, 411–428, 1994). The end-functionalized PVP can be silanated by the reaction described previously for the synthesis of trimethoxysilylalkyl m-PEO carbamate.

b) Silanation of PHEMA, PVA, and dextran can be achieved by the previously described method for the synthesis of trimethoxysilylalkyl m-PEO carbamate. Since PHEMA, PVA, and dextran possess more than one —OH groups in each polymer. the molar ratio of the reactants can be controlled so that only one silane group reacts with each polymer.

c) Silanation of PAA and PMA can be achieved by the previously described method for the synthesis of trimethoxysilylalkyl m-PEO succinylamide.

The following are examples of syntheses of silanated hydrophilic polymers. In these examples, there are no linking moieties, L. although the structures of Y would remain the same in the presence L.

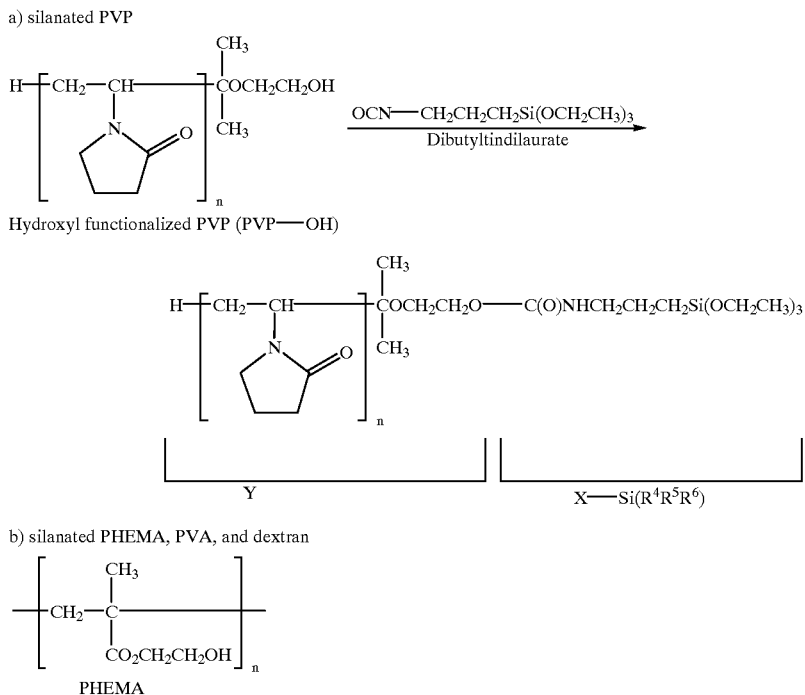

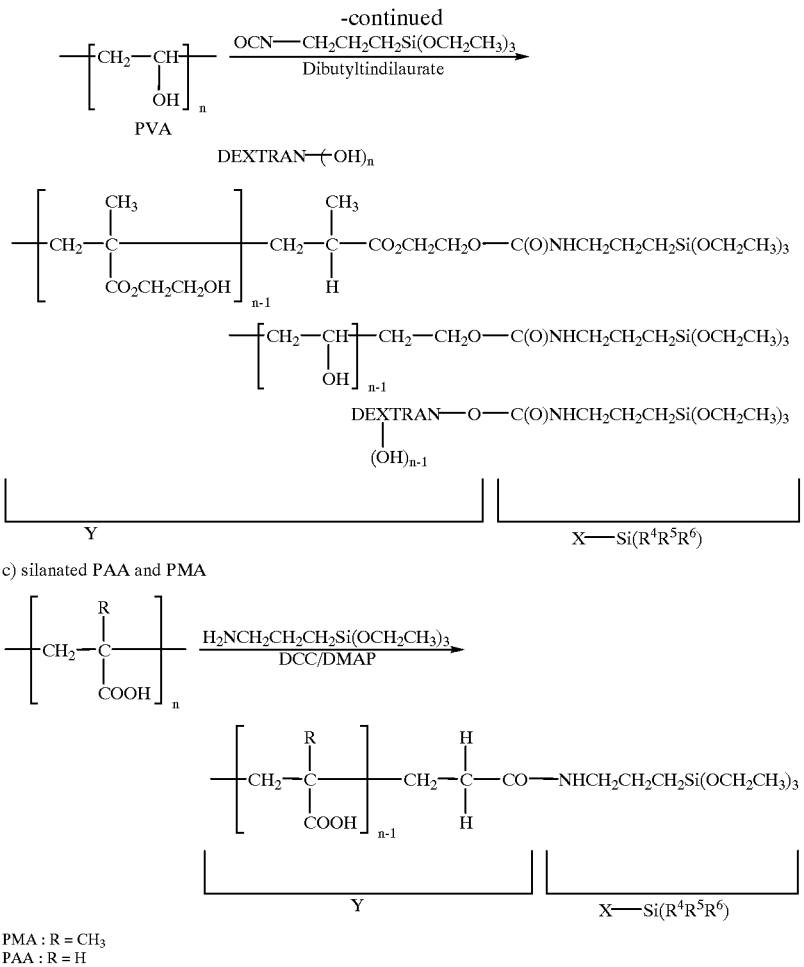

PMA : R = CH₃
PAA : R = H

Grafting of Silylated PEO Coupling Agents

In most preliminary studies glass was used as a model surface. Glass tubes (0.75 mm radius×100 mm length; Kimble, N.J.) were cleaned by soaking in chromic acid overnight and washing extensively in running distilled water. They were further washed three times with deionized distilled water for 10 minutes in an ultrasonic cleaner (Branson, Danbury Conn.).

Ethanol or methanol solutions of the silylated PEO coupling agents were made by dissolving the polymer in a 95:5 alcohol to water solution and adjusting the pH of the final solution to the desired pH with concentrated HCl. Typically, the concentration of the silanated polymer was varied from 0.001 mg/ml to 4 mg/ml. The time for polymer adsorption and subsequent grafting to the surface was varied from 1 min up to 60 min. Our preliminary experiments showed that 1 min of adsorption was enough. But, for all subsequent experiments, the adsorption time of 30 min was used.

The glass tubes were first filled with a 95:5 alcohol to water solution and the polymer solution was introduced into the tube using a syringe. After the desired reaction time, the tubes were rinsed three times with 5 ml of 95:5 alcohol to water. The washed tubes were then dried in vacuo for 1 hour at 50° C. Each tube was then washed by soaking in 1% SDS solution overnight to remove ungrafted PEO and rinsed extensively with distilled deionized water. The efficiency of the PEO grafting was examined by fibrinogen adsorption experiment. As more PEO chains are grafted to the surface, less fibrinogen adsorption occurs.

Effect of pH on grafting

To examine the effect of pH on the PEO grafting efficiency, the pH of the solution was varied from 2 to 5 by adding concentrated HCl. The concentration of triethoxysilylpropyl m-PEO carbamate was varied up to 4 mg/ml. Polymer was allowed to adsorb to glass and interact with the surface for 30 min. The fibrinogen adsorption study showed that PEO was grafted to the surface regardless of pH ranging from 2 to 5. For all subsequent experiments, however, pH 2 was employed due to the ease of solubilization of silanated PEO at the lower pH.

Effect of polymer concentration on grafting

The concentration of triethoxysilylpropyl m-PEO carbamate was varied from 0.001 mg/ml to 4 mg/ml. The adsorption of the polymer to glass was kept at 30 min. for these experiments. FIG. 9 shows that fibrinogen adsorption was minimized when the polymer concentration in the adsorption solution was 0.1 mg/ml. The polymer concentration at 0.1 mg/ml of higher will result in PEO grafting in such a way that the fibrinogen adsorption is minimized.

Comparison of two different types of silanated PEO

Solutions of triethoxysilylpropyl m-PEO carabmate and trimethoxysilylpropyl-thioundecyl m-PEO carbamate 1,6-dicarbamatohexane were prepared. As shown in FIG. 10, both silanated PEO, when grafted to glass surfaces, were able to prevent fibrinogen absorption effectively. No significant differences in the surface concentrations were observed between the two different types of silanated PEO, as shown in FIG. 10. The control consisted of surfaces treated with same manner as samples only without silanated PEO.

Grafting of silanated PEO on metallic stent

Triethoxysilylpropyl m-PEO carbamate was grafted to the nitinol stents using the polymer concentration of 1 mg/ml at pH 2 and adsorption time of 30 min. The surface fibrinogen concentrations on control and PEO-grafted stents were measured to examine the efficiency of the grafted PEO in preventing protein adsorption. As shown in FIG. 11, the surface fibrinogen concentration on the PEO-grafted stent was reduced more than 50% compared to that on the control stent. FIG. 11 clearly shows the effectiveness of the silanated PEO for grafting to the nitinol stent.

From the foregoing description, various modifications and changes in the composition and method will occur to those skilled in the art. All such modifications coming within the scope of the appended claims are intended to be included therein.

What is claimed is:

1. A method of grafting hydrophilic polymers to a surface of an article comprising the steps of:
    (a) providing an article having a plurality of hydroxyl or oxide groups attached to a surface of said article;
    (b) exposing said surface to a silanated hydrophilic polymer that has the structure:

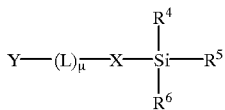

wherein at least one of said $R^4$, $R^5$, and $R^6$ is a hydrolyzable group each containing 1 to 6 carbon atoms, with the other(s) being nonhydrolyzable alkyl groups each containing 1 to 4 carbons, X is selected from an alkyl group, aryl group that is unsubstitued or substituted by one or more $C_{1-20}$ alkyl groups, L is a linking moiety having one or more linking groups that is selected from amide (—C(O)NH—), ester (—C(O)O—), urea (—NHC(O)NH—), urethane (—OC(O)NH—), ether (—O—), thioether(—S—), thiocarbamate (—OC(S)NH—), amine (—NH—), and mixture thereof provided that when L comprises more than one linking group, each is separated from the next by —(CH$_2$)$_m$—, wherein m is an integer from 1 to 20, $\mu$ is 0 or 1, and Y is a hydrophilic polymer; and
    (c) hydrolyzing the silanated hydrophilic polymer to form a silane layer; and
    (d) curing the silane layer to cause the silane layer to be covalently bonded to the surface of the article.

2. The method of claim 1 wherein the article is made of inorganic material or metal.

3. The method of claim 1 wherein the surface is made from a material selected from the group consisting of stainless steel, titanium, titanium nickel alloys, titanium aluminum vanadium alloys, tantalum, aluminum, chrome-cobalt alloys, pyrolytic carbon, glass, ceramics and mixtures thereof.

4. A method of grafting hydrophilic polymers to a surface of an article comprising the steps of:
    (a) providing an article having a plurality of hydroxyl or oxide groups on a surface thereof;
    (b) exposing said surface to a silanated hydrophilic polymer selected from the group consisting of 8-(m-PEO)octyltrimethoxysilane, 8-(m-PEO)octyltriethoxysilane, 4-(m-PEO)butyltrimethoxysilane, 4-(m-PEO)butyltriethoxysilane, 3-(m-PEO)propyltrimethoxysilane, 3-(m-PEO)propyltriethoxysilane, triethoxysilylpropyl m-PEO carbamate, trimethoxysilylpropyl m-PEO carbamate, trimethoxysilylpropylureidododecylureido m-PEO carbamate, triethoxysilylpropylureidodecylureido m-PEO carbamate, triethoxysilylpropyluredecylureido m-PEO carbamate, trimethoxysilylpropyluredodecylureido m-PEO carbamate, trimethoxysilylpropylthioundecyl m-PEO 1,6-dicarbamatohexane, trimethoxysilylpropylthioundecyl m-PEO 1,4-dicarbamatobutane, trimethoxysilylpropylthioundecyl m-PEO 1,8-dicarbamatooctane, trimethoxysilylpropylthioundecyl m-PEO 1,12-dicarbamatododecane, triethoxysilylpropylthioundecyl m-PEO 1,6-dicarbamatohexane, triethoxysilylpropylthioundecyl m-PEO, 1,4-dicarbamatobutane, triethoxysilylpropylthioundecyl m-PEO 1,8-dicarbamatooctane, triethoxysilylpropylthioundecyl m-PEO 1,12-dicarbamatododecane, and mixtures thereof;
    (c) hydrolyzing the silanated hydrophilic polymer to form a silane layer; and
    (d) curing the silane layer to cause the silane layer to be covalently bonded to the surface of the article.

5. The method of claim 1 wherein $R^4$, $R^5$, and $R^6$ are each a hydrolyzable group selected from the group consisting of methoxy, ethoxy, propoxy, butoxy, phenoxy, pentoxy, bromide, chloride, and iodide.

6. The method of claim 1 wherein X is a nonhydrolyzable group selected from the group containing methyl, ethyl, propyl butyl, hexyl, octyl, benzyl, and cyclohexyl.

7. The method of claim 1 wherein L is a linkage moiety and also extendible, hydrophobic moiety having one or more linking groups that connect linear hydrophobic hydrocarbons selected from the group consisting of hexyl, octyl, decyl, undecyl, and dodecyl, by the linkages selected from the group consisting of urethane, urea and ether.

8. The method of claim 6 wherein L is linear hydrophobic linking moiety consisting of 4-diisocyantobutane, 1,6-diisocyanatohexane, 1,4-diisocyanatobenzene, 1,8-diisocyanatooctane, 1,12-diisocyanatododecane, 10-undecen-1-ol, 9-decen-1-ol, 1,12-diaminododecane, 1,10-diaminodecane, 1,9-diaminononane, 1,8-diaminooctane, or mixtures thereof.

9. The method of claim 1 wherein step (d) forms a biocompatible surface that has a protein adsorption affinity of less than about 0.10 $\mu$g/cm$^2$.

10. The method of claim 1 wherein Y is polyethylene oxide.

11. The method of claim 1 wherein Y is selected from the group consisting of poly(vinyl pyrrolidone), poly(methacrylic acid), poly(acrylic acid), poly(hydroxyethylmethacrylate), and poly(vinyl alcohol).

12. A device having a biocompatible surface that has hydrophilic polymers grafted onto the surface and having been fabricated by a process comprising the steps of:
    (a) providing a device having a plurality of hydroxyl or oxide groups on a surface thereof;
    (b) exposing said surface to a silanated hydrophic polymer selected from the group consisting of the group containing 8-(m-PEO)octyltrimethoxysilane, 8-(m-PEO)octyltriethoxysilane, 4-(m-PEO)butyltrimethoxysilane, 4-(m-PEO)butyltriethoxysilane, 3-(m-PEO)propyltrimethoxysilane, 3-(m-PEO)propyltriethoxysilane, triethoxysilylpropyl m-PEO carbamate, trimethoxysilylpropyl m-PEO carbamate, trimethoxysilylpropylureidododecylureido m-PEO carbamate, triethoxysilylpropylureidodecylureido m-PEO carbamate, triethoxysilylpropylureidecylureido m-PEO carbamate, trimethoxysilylpropylureidodecylureido m-PEO carbamate, trimethoxysilylpropylthioundecyl m-PEO 1,6-dicarbamatohexane, trimethoxysilylpropylthioundecyl m-PEO, 1,4-dicarbamatobutane, trimethoxysilylpropylthioundecyl m-PEO 1,8-dicarbamatooctane, trimethoxysilylpropylthioundecyl m-PEO 1,12-dicarbamatododecane, triethoxysilylpropylthioundecyl m-PEO 1,16-dicarbamatohexane, triethoxysilylpropylthioundecyl m-PEO, 1,4-dicarbamatobutane, triethoxysilylpropylthioundecyl m-PEO 1,8-dicarbamatooctane, triethoxysilylpropylthioundecyl m-PEO 1,12-dicarbamatododecane, and mixtures thereof: and (c) curing the silane layer to cause the silane layer to be covalently bonded to the surface of the device.

13. A method of grafting hydrophilic polymers to a surface of an article comprising the steps of:

(a) providing an article having a plurality of hydroxy or oxide groups attached to a surface of said article;

(b) exposing said surface to trichlorovinylsilane to form a silane layer that is covalently bound to the surface; and (c) exposing the silane layer to a hydrophilic polymer selected from the group consisting of poly(ethylene oxide) (PEO), polyhydroxyethylmethacrylate (PHEMA), PEO-containing block copolymers, and mixtures thereof and causing the silane layer to react with the hydrophilic polymer to covalently bond to the silane layer.

14. A device having a biocompatible surface that has hydrophilic polymers grafted onto the surface and having been fabricated by a process comprising the steps of:

(a) providing a device having a plurality of hydroxyl or oxide groups attached to a surface of said device;

(b) exposing said surface to trichlorovinylsilane to form a silane layer that is covalently bound to the surface wherein the silane layer comprises a plurality of vinyl groups; and (c) exposing the silane layer to a hydrophilic polymer of poly(ethylene oxide) and causing the silane layer to react with poly(ethylene oxide) to covalently bond to the silane layer.

15. The method of claim 13, wherein the silane layer comprises a plurality of vinyl groups.

16. The method of claim 13 wherein the hydrophilic polymer is poly(ethylene oxide).

* * * * *